United States Patent [19]

Kusaba et al.

[11] Patent Number: 5,563,159
[45] Date of Patent: Oct. 8, 1996

[54] DITHIOCARBONIMIDE DERIVATIVES USEFUL AS ACARICIDAL, FUNGICIDAL, AND INSECTICIDAL AGENTS

[75] Inventors: Tomoyuki Kusaba, Toyonaka; Tadashi Ohsumi, Nishinomiya; Tsuguhiro Katoh, Sanda; Makoto Fujimura, Toyonaka; Norio Kimura, Takarazuka; Kazuya Ujihara, Takarazuka; Kimitoshi Umeda, Takarazuka, all of Japan

[73] Assignee: Sumitomo Chemical Company, Limited, Osaka-fu, Japan

[21] Appl. No.: 353,355

[22] Filed: Dec. 2, 1994

[30] Foreign Application Priority Data

| Dec. 3, 1993 | [JP] | Japan | 5-304034 |
| Mar. 16, 1994 | [JP] | Japan | 6-045724 |
| Jun. 29, 1994 | [JP] | Japan | 6-147928 |
| Sep. 19, 1994 | [JP] | Japan | 6-223310 |

[51] Int. Cl.$^6$ .......... A01N 37/52; A01N 43/40; C07C 381/00; C07D 213/76
[52] U.S. Cl. .......... 514/346; 514/247; 514/272; 514/275; 514/359; 514/362; 514/363; 514/370; 514/377; 514/380; 514/383; 514/398; 514/508; 544/224; 544/239; 544/332; 546/292; 548/135; 548/138; 548/194; 548/214; 548/233; 548/255; 548/264.8; 548/326.5
[58] Field of Search .......... 558/2; 514/508, 514/346; 546/292

[56] References Cited

U.S. PATENT DOCUMENTS 4,824,854  4/1989  Baker et al. .......... 514/346

FOREIGN PATENT DOCUMENTS

| 0378308 | 1/1990 | European Pat. Off. |
| 0582902 | 7/1993 | European Pat. Off. |
| 9107385 | 5/1991 | WIPO |
| 9117152 | 11/1991 | WIPO |
| 9307116 | 3/1995 | WIPO |

*Primary Examiner*—Johann Richter
*Assistant Examiner*—Michael G. Ambrose
*Attorney, Agent, or Firm*—Birch, Stewart, Kolasch & Birch LLP

[57] ABSTRACT

There is disclosed a dithiocarbonimide derivative of the formula:

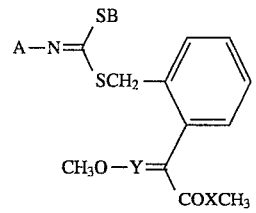

wherein B is a $C_1$–$C_6$ alkyl group; X is an NH group or an oxygen atom and Y is a nitrogen atom or a CH group, A is a phenyl group, a heterocyclic group, an alkyl group, an alkenyl group, an alkynyl group, a cycloalkyl group, a cycloalkenyl group, a bicycloalkyl group or a tricycloalkyl group, all of which may be substituted. Also disclosed are a fungicidal/insecticidal/acaricidal agent containing the dithiocarbonimide derivative as an active ingredient, an intermediate for use in the production of the dithiocarbonimide derivative, and a process for producing the dithiocarbonimide derivative from the intermediate.

16 Claims, No Drawings

DITHIOCARBONIMIDE DERIVATIVES USEFUL AS ACARICIDAL, FUNGICIDAL, AND INSECTICIDAL AGENTS

FIELD OF THE INVENTION

The present invention relates to dithiocarbonimide derivatives, fungicidal/insecticidal/acaricidal agents containing the derivatives as an active ingredient, an intermediate for use in the production of the derivatives and processes for producing the derivatives from the intermediates.

DESCRIPTION OF THE RELATED ART

In WO 93/07 116, there is described that certain kinds of oxime derivatives are used as an active ingredient of fungicides. However, these oxime derivatives are not necessarily suitable as an active ingredient of agricultural/horticultural fungicides.

SUMMARY OF THE INVENTION

Under these circumstances, it is an object of the present invention to provide a good agricultural/horticultural fungicide.

That is, the present invention provides a dithiocarbonimide derivative of the formula I:

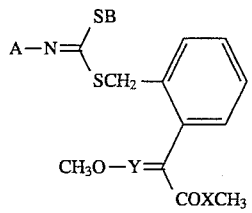

wherein B is a $C_1$–$C_6$ alkyl group; when X is an NH group and Y is a nitrogen atom, A is a phenyl group, a heterocyclic group, an alkyl group, an alkenyl group, an alkynyl group, a cycloalkyl group, a cycloalkenyl group, a bicycloalkyl group or a tricycloalkyl group, all of which may be substituted; when X is an oxygen atom and Y is a nitrogen atom or a CH group, A is a group of the formula:

R—CH$_2$CH$_2$— wherein R is a tert-butyl group, an isopropyl group or a phenyl group which may be substituted with at least one group selected from a halogen atom, a $C_1$–$C_4$ alkyl group, a $C_1$–$C_4$ alkylthio group, a $C_1$–$C_4$ haloalkyl group, a $C_1$–$C_4$ haloalkoxy group and a cyano group, or alternatively A is a 2-ethoxypyridine-5-yl group, a 4-n-propylphenyl group or a 4-ethoxyphenyl group.

It is another object of the present invention to provide an agricultural/horticultural fungicide, an insecticide and an acaricide, each of which contains a dithiocarbonimide derivative of the formula I as an active ingredient.

It is still another object of the present invention to provide processes for producing a dithiocarbonimide of the formula I.

It is still another object of the present invention to provide an intermediate of the formula II:

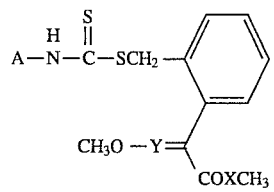

wherein when X is an NH group and Y is a nitrogen atom, A is a phenyl group, a heterocyclic group, an alkyl group, an alkenyl group, an alkynyl group, a cycloalkyl group, a cycloalkenyl group, a bicycloalkyl group or a tricycloalkyl group, all of which may be substituted; when X is an oxygen atom and Y is a nitrogen atom or a CH group, A is a group of the formula:

R—CH$_2$CH$_2$— wherein R is a tert-butyl group, an isopropyl group or a phenyl group which may be substituted with at least one group selected from a halogen atom, a $C_1$–$C_4$ alkyl group, a $C_1$–$C_4$ alkylthio group, a $C_1$–$C_4$ haloalkyl group, a $C_1$–$C_4$ haloalkoxy group and a cyano group, or alternatively A is a 2-ethoxypyridine-5-yl group, a 4-n-propylphenyl group or a 4-ethoxyphenyl group.

DETAILED DESCRIPTION OF THE INVENTION

The dithiocarbonimide derivatives of the present invention are effective against various crop plant diseases, insects and acarines.

First, the following will describe on the dithiocarbonimide derivative of the formula I.

The group for A in the formula I includes a phenyl group or a heterocyclic group, both of which may be optionally substituted. The substituents of the phenyl group or the heterocyclic group may be the same or different, examples of which include a $C_1$–$C_6$ alkyl group (e.g. a methyl group, an ethyl group, an n-propyl group, an isopropyl group, an n-butyl group, a tert-butyl group, etc.), a halogen atom (e.g. a fluorine atom, a chlorine atom, a bromine atom, etc.), a $C_1$–$C_6$ alkoxy group (e.g. a methoxy group, an ethoxy group, an n-propyloxy group, an isopropyloxy group, an n-butyloxy group, etc.), a phenoxy group, a $C_1$–$C_6$ alkylthio group (e.g. a methylthio group, an ethylthio group, an n-propylthio group, an n-butylthio group, etc.), an ($C_1$–$C_6$)-alkyloxycarbonyl group (e.g. a methoxycarbonyl group, an ethoxycarbonyl group, etc.), a cyano group, a nitro group, a $C_1$–$C_6$ haloalkyl group (e.g. a trifluoromethyl group, etc.), a $C_1$–$C_6$ haloalkoxy group (e.g.. a trifluoromethoxy group, etc.), a methylenedioxy group which may substituted with a fluorine atom (e.g. a methylenedioxy group, a difluoromethylenedioxy group, etc.) and the like.

The heterocyclic group represented by A which may be substituted may be a 5- or 6-membered aromatic heterocyclic group, examples of which include a pyridyl group, a pyrimidinyl group, a pyridazinyl group, a pyrazolyl group, an imidazolyl group, an oxazolyl group, a thiazolyl group, an isothiazolyl group, a triazolyl group, a thiadiazolyl and the like.

Specific examples of the heterocyclic group include a 2-, 3- or 4-pyridyl group, a 2-, 4- or 5-pyrimidinyl group, a 3- or 4-pyridazinyl group, a 3-, 4- or 5-pyrazolyl group, a 2-or 4-imidazolyl group, a 2-, 4-or 5-oxazolyl group, a 2-, 4- or 5-thiazolyl group, a 3-, 4-or 5-isothiazolyl group, a 1,2,4-triazol-3-yl group, a 1,3,4-thiadiazol-2-yl group and the like.

Furthermore, the group A represents an alkyl group, an alkenyl group, an alkynyl group, a cycloalkyl group, a cycloalkenyl group, a bicycloalkyl group or a tricycloalkyl group, all of which may be optionally substituted.

For the group A, the alkyl group, alkenyl group, alkynyl group, cycloalkyl group, cycloalkenyl group, bicycloalkyl group or tricycloalkyl group, all of which may be substituted is preferably a $C_1$–$C_{20}$ alkyl group, a $C_2$–$C_{20}$ alkenyl group, a $C_2$–$C_{20}$ alkynyl group, a $C_3$–$C_{20}$ cycloalkyl group, a $C_5$–$C_{20}$ cycloalkenyl group, a $C_4$–$C_{20}$ bicycloalkyl group or a $C_4$–$C_{20}$ tricycloalkyl group, all of which may be substituted.

More preferably, these groups are a $C_1$–$C_{10}$ alkyl group, a $C_2$–$C_{10}$ alkenyl group, a $C_2$–$C_{10}$ alkynyl group, a $C_3$–$C_{10}$ cycloalkyl group, a $Ch_5$–$C_{10}$ cycloalkenyl group, a $C_4$–$C_{10}$ bicycloalkyl group or a $C_4$–$C_{10}$ tricycloalkyl group, all of which may be substituted.

The substituents on the alkyl group, alkenyl group, alkynyl group, cycloalkyl group, cycloalkenyl group, bicycloalkyl group or tricycloalkyl group may be the same or different and are three or less groups selected from the group of a methoxy group, an ethoxy group, an n-propoxy group, an isopropoxy group, an n-butoxy group, a t-butoxy group, a trifluoromethoxy group, a 2,2,2-trifluoroethoxy group, a 2,2,2,2',2',2'-hexafluoroisopropoxy group, a fluorine atom, a chlorine atom, a bromine atom, an iodine atom, a cyano group, a methylthio group, an ethylthio group, a phenyl group, a phenoxy group, a phenylthio group, a 2-furyl group, a 2-thienyl group, a 1 imidazolyl group, a 2-imidazolyl group, a 2-pyridyl group, a 3-pyridyl group, a 4-pyridyl group, a cyclopropyl group, a cyclobutyl group, a cyclopentyl group, a cyclohexyl group, a tetrahydrofuryl group, a tetrahydropyranyl group and a 4-morpholinyl group, wherein the phenyl group, phenoxy group, phenylthio group, 2-furyl group, 2-thienyl group, 1-imidazolyl group, 2-imidazolyl group, 2-pyridyl group, 3-pyridyl group, 4-pyridyl group, cyclopropyl group, cyclobutyl group, cyclopentyl group, cyclohexyl group, tetrahydrofuryl group, tetrahydropyranyl group and 4-morpholinyl group may be substituted with three or less groups which are same or different and are selected from the group of a methyl group, an ethyl group, an n-propyl group, an isopropyl group, a trifluoromethyl group, a methoxy group, an ethoxy group, an n-propoxy group, an isopropoxy group, a trifluoromethoxy group, a fluorine atom, a chlorine atom, a bromine atom, an iodine atom, a cyano group, a nitro group, a methylthio group and an ethylthio group.

Specific examples of the $C_1$–$C_{10}$ alkyl group which may be substituted are a methyl group, an ethyl group, a propyl group, a butyl group, a pentyl group, a hexyl group, a heptyl group, an octyl group, a nonyl group, a decyl group, 1-methylethyl group, 1-methylpropyl group, 2-methylpropyl group, a 1,1-dimethylethyl group, a 1-methylbutyl group, a 1-ethylpropyl group, a 2-methylbutyl group, a 3-methylbutyl group, a 2,3-dimethylbutyl group, a 1,3-dimethylbutyl group, a 3,3-dimethylbutyl group, a 1-methylpentyl group, a 1-ethylpentyl group, a 1-methylhexyl group, a 2-ethylhexyl group or a 1,5-dimethylhexyl; or alternatively, a group of the formula:

R is a phenyl group which may be substituted with a halogen atom (e.g. a chlorine atom, a bromine atom, a fluorine atom), a $C_1$–$C_4$ alkyl group (e.g. a methyl group, an ethyl group, an isopropyl group, tert-butyl group), a $C_1$–$C_4$ alkoxy group (e.g. a methoxy group, an ethoxy group, an isopropoxy group, a tert-butoxy group), a $C_1$–$C_4$ alkylthio group (e.g. a methylthio group, an ethylthio group), a $C_1$–$C_4$ haloalkyl group (e.g. a trifluoromethyl group) or a $C_1$–$C_4$ haloalkoxy group (e.g. a trifluoromethoxy group, a difluoromethoxy group, a 2,2,2-trifluoroethoxy group, a 1,1,2,2-tetrafluoroethoxy group).

Among the $C_1$–$C_{10}$ alkyl group which may be substituted, more preferable groups are a group of the formula:

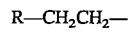

wherein R is a tert-butyl group, an isopropyl group or a phenyl group which may be substituted with a halogen atom (e.g. a chlorine atom, a bromine atom, a fluorine atom), a $C_1$–$C_4$ alkyl group (e.g. a methyl group, an ethyl group, an isopropyl group, tert-butyl group), a $C_1$–$C_4$ alkoxy group (e.g. a methoxy group, an ethoxy group, an isopropoxy group, a tert-butoxy group), a $C_1$–$C_4$ alkylthio group (e.g. a methylthio group, an ethylthio group), a $C_1$–$C_4$ haloalkyl group (e.g. a trifluoromethyl group) or a $C_1$–$C_4$ haloalkoxy group (e.g. a trifluoromethoxy group, a difluoromethoxy group, a 2,2,2-trifluoroethoxy group, a 1,1,2,2-tetrafluoroethoxy group).

Examples of the alkenyl group which may be substituted are an allyl group and a 2-methylallyl group.

Examples of the alkynyl group which may be substituted are a propargyl group.

Examples of the cycloalkyl group which may be substituted are a cyclopropyl group, a cyclobutyl group, a cyclopentyl group, a cyclohexyl group, a cycloheptyl group, a cyclooctyl group and a cyclodecyl group.

Examples of the cycloalkenyl group which may be substituted are a cyclopentenyl group and a cyclohexenyl group.

Examples of the bicycloalkyl group which may be substituted are an exo-2-norbornyl group and an endo-2-norbornyl group.

Examples of the tricycloalkyl group which may be substituted are a 1-adamantyl group and a 2-adamantyl group.

B is a $C_1$–$C_6$ alkyl group (e.g. a methyl group, an ethyl group, an n-propyl group, an isopropyl group, an n-butyl group, etc.), and preferably B is a methyl group.

Among the dithiocarbonimide derivatives of the present invention, those in which X is a NH group are preferred.

The following will describe the production processes for the dithiocarbonimide derivative of the present invention.

Process A:

The dithiocarbonimide derivative of the formula I wherein X is a NH group; Y is a nitrogen atom; and A is a phenyl group, a heterocyclic group, an alkyl group, an alkenyl group, alkynyl group, a cycloalkyl group, a cycloalkenyl group, a bicycloalkyl group or a tricycloalkyl group, all of which may be substituted, can be produced by reacting a compound of the formula I wherein X is an oxygen atom; and Y and A are each as defined above, with methylamine.

The reaction temperature is usually in the range of from 0° C. to 30° C.

The amount of the methylamine is usually in the range of 1 mol or more, based on 1 mol of the compound of the formula I to be used as the starting material in the reaction.

Examples of the solvent to be used include alcohols such as methanol, ethanol and isopropanol; aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane and chlorobenzene; ethers such as diethyl ether, diisopropyl ether, dioxane, tetrahydrofuran and ethyleneglycol dimethyl ether; amides such as formamide, N,N-dimethylformamide and N,N-dimethylacetamide; sulfur compounds such as dimethyl sulfoxide and sulfolane; water, or mixtures thereof.

After the completion of the reaction, the reaction product can be subjected to an ordinary post-treatment such as concentration, and may be purified, if necessary, by an operation such as column chromatography or recrystallization, to give the desired compound.

Process B:

The dithiocarbonimide derivative of the formula I wherein B is a $C_1$–$C_6$ alkyl group; when X is an NH group and Y is a nitrogen atom, A is fi phenyl group, a heterocyclic group, an alkyl group, an alkenyl group, an alkynyl group, a cycloalkyl group, a cycloalkenyl group, a bicycloalkyl group or a tricycloalkyl group, all of which may be substituted; when X is an oxygen atom and Y is a nitrogen atom or a CH group, A is a group of the formula:

$$R—CH_2—CH_2—$$

wherein R is a tert-butyl group, an isopropyl group or a phenyl group which may be substituted with at least one group selected from a halogen atom, a $C_1$–$C_4$ alkyl group, a $C_1$–$C_4$ alkylthio group, a $C_1$–$C_4$ haloalkyl group, a $C_1$–$C_4$ haloalkoxy group and a cyano group, or alternatively A is a 2-ethoxypyridine-5-yl group, a 4-n-propylphenyl group or a 4-ethoxyphenyl group, can be produced by reacting a dithiocarbamate derivative of the formula II:

$$A-\underset{H}{N}-\overset{\overset{S}{\|}}{C}-SCH_2-\underset{\underset{COXCH_3}{|}}{\underset{CH_3O-Y=}{\bigcirc}}$$

wherein A, X and Y are each as defined above, with a compound of the formula III:

B-W wherein B is as defined above and W is a chlorine atom, a bromine atom, an iodine atom, a mesyloxy group or a tosyloxy group.

The reaction temperature is usually in the range of from 0° C. or the solidifying point of the solvent to be used to the boiling point of the solvent or 150° C., preferably from 10° C. to 30° C.

The reaction is usually conducted in the presence of a base, examples of which include hydroxides of alkali metals, such as sodium hydroxide; carbonates of alkali metals, such as potassium carbonate; and hydrides of alkali metals, such as sodium hydride.

The amounts of the compound of the formula III and the base to be optionally used are usually in the range of from 1 to 2 tools, respectively, based on 1 tool of the dithiocarbamate derivative of the formula II.

Examples of the solvent to be used include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane and chlorobenzene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; nitro compounds such as nitrobenzene; nitriles such as acetonitrile and isobutyronitrile; amides such as formamide, N,N-dimethylformamide and N,N-dimethylacetamide; sulfur compounds such as dimethyl sulfoxide and sulfolane. When no flammable base such as sodium hydride is used, water can be used as the solvent. Further, the above solvents can be used alone or in combination.

After the completion of the reaction, the reaction product can be subjected to an ordinary post-treatment such as organic solvent extraction, rinsing and concentration, and may be purified, if necessary, by an operation such as column chromatography or recrystallization, to give the desired compound.

Process C:

Furthermore, the dithiocarbonimide derivative of the formula I wherein X, Y, A and B are each as defined above, can be produced by reacting a dithiocarbamate compound of the formula IV:

$$A-NH-\overset{\overset{S}{\|}}{C}-S-B$$

wherein A and B are each as defined above, with a compound of the formula V:

$$WCH_2-\underset{\underset{COXCH_3}{|}}{\underset{CH_3O-Y=}{\bigcirc}}$$

wherein X, Y and W are each as defined above.

The compound of the formula V can be produced by the methods described in JP-A 246268/1991, JP-A 30463/1988, WO-9307 116 and DE-4030038.

The reaction temperature is usually in the range of from 0° C. or the solidifying point of the solvent to be used to the boiling point of the solvent or 150° C., preferably from 10° C. to 30° C.

The reaction is usually conducted in the presence of a base, examples of which include hydroxides of alkali metals, such as sodium hydroxide; carbonates of alkali metals, such as potassium carbonate; and hydrides of alkali metals, such as sodium hydride.

The amounts of the compound of the formula V and the base to be optionally used are usually in the range of from 1 to 2 tools, respectively, based on 1 mol of the dithiocarbamate compound of the formula IV.

Examples of the solvent to be used include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane and chlorobenzene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitro compounds such as nitromethane and nitrobenzene; nitriles such as acetonitrile and isobutyronitrile; amides such as formamide, N,N-dimethylformamide and N,N-dimethylacetamide; sulfur compounds such as dimethyl sulfoxide and sulfolane.

When no flammable base such as sodium hydride is used, water can be used as the solvent. Further, the above solvents can be used alone or in combination.

After the completion of the reaction, the reaction product can be subjected to an ordinary post-treatment such as organic solvent extraction, rinsing and concentration, and may be purified, if necessary, by an operation such as column chromatography or recrystallization, to give the desired compound.

Process D:

The dithiocarbamate derivative of the formula II can be produced by reacting a salt of the dithiocarbonimide derivative of the formula VI:

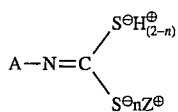

wherein A is as defined above, $Z^⊕$ is an alkali metal ion or an ammonium ion between a tertiary amine and a hydrogen atom and n is an integer of 1 or 2, with a compound of the formula V.

Examples of the tertiary amine are triethylamine, pyridine, N,N-dimethylaniline, tributylaniline and N-methylmorpholine; and examples of the alkali metal are sodium and potassium.

The reaction temperature is usually in the range of from 0° C. or the solidifying point of the solvent to be used to the boiling point of the solvent or 150° C., preferably from 10° to 30° C.

The amount of the compound of the formula V is in the range of from 1 to 2 tools, based on 1 mol of a salt of the dithiocarbonimide of the formula VI.

Examples of the solvent to be used include aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane and chlorobenzene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitro compounds such as nitromethane and nitrobenzene; nitriles such as acetonitrile and isobutyronitrile; amides such as formamide, N,N-dimethylformamide and N,N-dimethylacetamide; sulfur compounds such as dimethyl sulfoxide and sulfolane; or water. Further, the above solvents can be used alone or in combination.

After the completion of the reaction, the reaction product can be subjected to an ordinary post-treatment such as organic solvent extraction, rinsing and concentration, and may be purified, if necessary, by an operation such as chromatography or recrystallization, to give the dithiocarbamate derivative of the formula II.

Process E:

In addition, the dithiocarbamate compound of the formula IV can be produced by reacting a salt of the dithiocarbonimide of the formula VI with the corresponding compound of the formula III.

The reaction temperature is usually in the range of from 0° C. or the solidifying point of the solvent to be used to the boiling point of the solvent or 150° C., preferably from 10° C. to 30° C.

The amount of the compound of the formula III is usually in the range of from 1 to 2 mols, based on 1 tool of a salt of the dithiocarbonimide of the formula VI.

Examples of the solvent to be used include alcohols such as methanol, ethanol and isopropanol; aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloromethane and chlorobenzene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitro compounds such as nitromethane and nitrobenzene; nitriles such as acetonitrile and isobutyronitrile; amides such as formamide, N,N-dimethylformamide and N,N-dimethylacetamide; sulfur compounds such as dimethyl sulfoxide and sulfolane; or water. Further, the above solvents can be used alone or in combination.

Process F:

The salt of the dithiocarbonimide of the formula VI can be produced by reacting an amine compound of the formula VII:

wherein A is as defined in the process A above, with carbon disulfide in the presence of a base.

Examples of the base include hydroxides of alkali metals, such as sodium hydroxide; carbonates of alkali metals, such as sodium carbonate and potassium carbonate; and hydrides of alkali metals, such as sodium hydride.

The reaction temperature is usually in the range of from 0° C. or the solidifying point of the solvent to be used to the boiling point of the solvent or 150° C., preferably from 10° C. to 30° C.

The amount of carbon disulfide is usually in the range of from 1 to 2 moles, based on 1 mole of the amine compound of the formula VII. The amount of the base is usually in the range of from 2 to 4 moles, but the base can be used as a solvent in a large excess amount.

Examples of the solvent to be used include aliphatic hydrocarbons such as hexane, heptane, ligroin and petroleum ether; aromatic hydrocarbons such as benzene, toluene and xylene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitro compounds such as nitromethane and nitrobenzene; nitriles such as acetonitrile and isobutyronitrile; amides such as formamide, N,N-dimethylformamide and N,N-dimethylacetamide; sulfur compounds such as dimethyl sulfoxide and sulfolane; alcohols such as methanol, ethanol and n-butanol; or water. Further, the above solvents can be used alone or in combination.

When the dithiocarbonimide of the present invention is used as an active ingredient of an agricultural/horticultural fungicide, it may be used as such without adding any other component, but it is usually mixed with solid carriers, liquid carders, surfactants and other auxiliary agents to formulate into dosage forms such as emulsifiable concentrates, wettable powders, suspensions, dusts or granules. These formulations contain the active ingredient in an amount of from 0.1% to 99.9% by weight, preferably from 1% to 90% by weight, based on the total weight of the formulation.

Examples of the solid carder include fine powders or granules of kaolin clay, attapulgite clay, bentonite, acid clay, pyroillite, talc, diatomaceous earth, calcite, corncob powder, walnut shell flour, urea, ammonium sulfate, synthetic hydrated silicon oxide or the like.

Examples of the liquid carder include aromatic hydrocarbons such as xylene and methylnaphthalene; alcohols such as isopropanol, ethylene glycol and cellosolve; ketones such as acetone, cyclohexanone and isophorone; vegetable oils such as soybean oil and cotton seed oil; dimethyl sulfoxide, acetonitrile, water and the like.

Examples of the surfactant used for emulsification, dispersion, wetting or the like include anionic surfactants such as alkyl sulfates, alkyl aryl sulfonates, dialkyl sulfosuccinate, polyoxyethylene alkyl aryl ether phosphate and formalin naphthalenesulfonate condensate; and nonionic surfactants such as polyoxyethylene alkyl ether, polyoxyethylene alkylpolyoxypropylene block copolymer and sorbitan fatty acid ester.

Examples of the auxiliary agent for formulation include lignin sulfonate, alginate, polyvinyl alcohol, gum arabic, CMC (carboxymethyl cellulose), PAP (isopropyl acid phosphate) and the like.

Examples of the application method for the dithiocarbonimide derivative of the present invention include application over stalk and leaves, soil treatment, seed disinfection and the like, but there can be used any application method which is usually used by those skilled in the art.

When the dithiocarbonimide derivative of the present invention is used as an active ingredient of a control agent for plant diseases, its application rate varies depending upon the kind of crop, kind of disease, severity of disease, form of the formulation, method and time of application, weather conditions and the like. The total mount of the compound as an active ingredient is usually in the range of from 0.01 to 50 g, preferably from 0.05 to 10 g per are.

Emulsifiable concentrates, wettable powders and suspensions are usually diluted with water to a concentration of from 0.0001% to 0.5%, preferably from 0.0005% to 0.2%. Dusts and granules are used as prepared.

The dithiocarbonimide derivative of the present invention can be used as an agricultural/horticultural fungicide for upland fields, paddy fields, orchards, tea fields, pastures, lawn grass fields or the like.

The fungicidal activity can be enhanced by mixing it with other agricultural/horticultural fungicides. Further, it can also be used after mixing with other fungicides, insecticides, acaricides, nematicides, herbicides, growth regulators for plants, fertilizers or the like.

Examples of the plant disease which can be controlled by the dithiocarbonimide derivative of the present invention include the following diseases:

rice blast (*Pyricularia oryzae*), brown spot (*Cochliobolus miyabeantis*) and rice sheath blight (*Rhizoctonia solani*) of rice;

powdery mildew (*Erysiphe graminis*), fusarium blight (*Gibberella zeae*), Rust (*Puccinia striiformis, P. graminis, P. recondita, P. hordei*), snow rot (*Typhula sp., Micronectriella nivalis*), loose smut (*Ustilago tritici, U. nuda*), bunt (*Tilletia caries*), eye spot (*Pseudocercosporella herpotrichoides*), leaf blotch (*Rhynchosporium secalis*), speckled leaf blotch (*Septoria tritici*) and glume blotch (*Leptosphaeria nodorum*) of wheat;

melanose (*Diaporthe citri*), scab (*Elisinoe fawcetti*), blue mold (*Penicillium digitatum*) and green mold (*P. italicum*) of citrus fruits;

blossom blight (*Sclerotinia mail*), canker (*Valsa mali*), powdery mildew (*Podosphaera leucotricha*), altanaria blotch (*Alternaria mali*) and scab (*Venturia inaequalis*) of apples;

scab (*Venturia nashicola, V. pirina*), black spot (*Alternaria kikuchiana*) and rust (*Gymnosporangium haraeanum*) of pear;

brown rot (*Sclerotinia cinerea*), scab (*Cladosporium carpophilum*) and phomopsis rot (*Phomopsis* sp.) of peach;

anthracnose (*Elsinoe ampelina*), ripe rot (*Glomerella cingulata*), powdery mildew (*Uncinula necator*), rust (*Phakopsora ampelopsidis*), black rot (*Guignardia bidwellii*) and downy mildew (*Plasmopara viticola*) of grape;

anthracnose (*Gloeosporium kaki*) and angular leaf spot (*Cercospora kaki, Mycosphaerella nawae*) of persimmon;

anthracnose (*Colletotrichum lagenarium*), powdery mildew (*Spaerotheca fuliginea*), gummy stem blight (*Mycosphaerella melonis*), fusarium wilt (*Fusarium oxysporum*), downy mildew (*Pseudoperonospora cubensis*), phytophthora rot (*Phytophthora* sp.) and dumping off (*Pythim* sp.) of cucumbers;

early blight (*Alternaria solani*), leaf mold (*Cladosporium fulvum*) and late blight (*Phytophthora infestans*) of tomato;

brown spot (*Phomopsis vexans*) and powdery mildew (*Erysiphe cichoraearum*) of egg plant;

alternaria leaf spot (*Alternaria japonica*) and white spot (*Cercosporella brasscicae*) of vegetables of Cruciferae;

rust (*Puccinia allii*) of leek, purple atain (*Cerocosporera kikuchii*), sphacelome scab (*Etsinoe glycines*) and pod and stem blight (*Diaporthe phaseolorum* var. *sojae*) of soybean, anthracnose (*Colletotrichum lindemthianum*) of kidney beans, leaf spot (*Mycosphaerella personatum*) and brown leaf spot (*Cercospora arachidicola*) of peanuts, powdery mildew (*Erysiphe pisi*) of pea, early blight (*Alternaria solani*) and late blight (*phytophthora infestans*) of potato, powdery mildew (*Sphaerotheca humuli*) of strawberry, net blister blight (*Exobasidium reticulatum*) and white scab (*Elsinoe leucospila*) of tea, brown spot (*Alternaria longipes*), powdery mildew (*Erysiphe cichoracearum*), anthracnose (*Colletotrichum tabacum*), downy mildew (*Peronospora tabacina*) and black shanke (*Phytophthora nicotianae*) of tobacco, cercospora leaf spot (*Cercospora beticola*) of sugar beet, black spot (*Diplocarpon rosae*) and powdery mildew (*Sphaerotheca pannosa*) of rose, leaf blight (*Septoria chrysanthemi-indici*) and rust (*Puccinia horiana*) of chrythasemum, gray mold (*Botrytis cinerea*) and sclerotinia rot (*Sclerotinia sclerotiorum*) of various crops.

When the dithiocarbonimide derivative of the present invention is used as an active ingredient of insecticides/acaricides, it may be used as such without adding any other component, but it is usually mixed with solid carriers, liquid carders, gaseous carriers, baits, and if necessary, surfactants and other auxiliary agents to formulate into dosage forms such as oil solutions, emulsifiable concentrates, wettable powders, flowables, granules, aerosols, fumigants (foggings), poison baits and the like.

These formulations usually contain the dithiocarbonimide derivative of the present invention as an active ingredient in an amount of 0.01% to 95% by weight, based on the total weight of the formulation.

Examples of the solid carrier used for formulation include fine powders or granules of clays (e.g. kaolin clay, diatomaceous clay, synthetic hydrated silicon oxide, Fubasami clay, bentonite, acid clay, etc.), talcs, ceramics, other inorganic minerals (e.g. sericite, quartz, sulfur, active carbon, calcium carbonate, hydrated silica, etc.), and commercial fertilizers (e.g. ammonium sulfate, ammonium phosphate, ammonium nitrite, urea, ammonium chloride, etc.).

Examples of the liquid carrier include water, alcohols (e.g. methanol, ethanol, etc.), ketones (e.g. acetone, methyl ethyl ketone, etc.), aromatic hydrocarbons (e.g. benzene, toluene, xylene, ethylbenzene, methylnaphthalene, etc.), aliphatic hydrocarbons (e.g. hexane, cyclohexane, kerosine, gas oil, etc.), esters (e.g. ethyl acetate, butyl acetate, etc.), nitriles (e.g. acetonitrile, isobutyronitrile, etc.), ethers (e.g. diisopropyl ether, dioxane, etc.), acid amides (e.g. N,N-dimethylformamide, N,N-dimethylacetamide, etc.), halogenated hydrocarbons (e.g. dichloromethane, trichloroethane, carbon tetrachloride, etc.), dimethyl sulfoxide, vegetable oils (e.g. soybean oil, cottonseed oil, etc.) and the like.

Examples of the gaseous carrier, i.e. propellent, include CFCs gas, butane gas, LPG (liquefied petroleum gas), dimethylether, carbon dioxide gas and the like.

Examples of the surfactant include alkyl sulfates, salts of alkyl sulfonates, alkyl aryl sulfonates, alkyl aryl ethers, polyoxyethylene compounds thereof, polyoxyethylene glycol ethers, polyhydric alcohol esters, sugar alcohol derivatives and the like.

Examples of the auxiliary agent for formulation, such as fixing agents and dispersing agents, include casein, gelatin, polysaccharides (e.g. starch powder, gum arabic, cellulose derivative, alginic acid, etc.), lignin derivatives, bentonite, sugars, synthetic water-soluble polymers (e.g. polyvinyl alcohol, polyvinyl pyrrolidone, polyacrylic acid, etc.) and the like.

Examples of the stabilizer include PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surfactants, fatty acids or esters thereof and the like.

Examples of the base material of the poison bait include bait components such as grain powder, vegetable oils, sugar and crystalline cellulose; antioxidants such as dibutylhydroxytoluene and nordihydroguaiaretic acid; preservatives such as dehydroacetic acid; substances for preventing erroneous ingestion such as red pepper powder; attractant flavors such as cheese flavor and onion flavor.

The formulations thus obtained are used as prepared or after diluted, for example, with water.

The formulations may be used after mixed with other insecticides, nematicides, acaricides, fungicides, herbicides, plant growth inhibitors, synergists, fertilizers, soil conditioners, animal feeds or the like, or may be used simultaneously with them.

When the dithiocarbonimide derivative of the present invention is used as an agricultural insecticide/acaricide, its application rate is usually 0.1 to 100 g per 10 ares.

Granules and dusts are applied as prepared.

When the dithiocarbonimide derivative of the present invention is used as an active ingredient of insecticides/acaricides, emulsifiable concentrates, wettable powders and flowables are usually diluted, for example, with water to a concentration of 0.1 to 500 ppm.

Oil solutions, aerosols, fog formulations and poison baits are applied as prepared.

The application rate and concentration of the formulations may be varied, i.e. optionally increased or decreased according to the type of formulation, time, place and method of application, kind of noxious insects, degree of dame and the like.

Examples of noxious insects against which the dithiocarbonimide derivative of the present invention exhibits insecticidal/acaricidal activity include:

Hemiptera:
  Delphacidae (leaf hoppers) such as *Laodelphax striatellus, Nilaparvata lugens* and *Sogatella fitrcifera;*
  Cicadelloidea (leaf hoppers) such as *Nephotettix cincticeps* and *Nephotettix virescens,* Aphidoidea (aphids), Pentatornidae (stink bugs), Aleyrodidae, Coccoidea (scale insects), Tingidac (lace bugs), Psyllidea (jumping plant-lices), etc.;
Lepidoptera:
Pyralidae such as *Chilo suppressalis, Cnaphalocrocis medinalis,* and india meal moth (*Pladia interpuctella*),
Nocutuiidae such as *Spodoptera litura, Pseudaletia separata* and *Mamestra brassicae,*
Pieridac such as *Pieris rapae crucivora,*
Tortricidae (bell months) such as *Adoxothyes, Carposina niponesis,* Lyonetiidae (leaf mining months), gypsy months, *Tricipursia* (looper), Agrothis spp. such as *Agrotis segetum, Agrotisipsilon, Heliothis* spp.,
*Plutella xylostella, Tinea translucens, Tincola bissellielta,* etc.;
Diptera:
Culex (house mosquitos) such as *Culex pipiens pallens* and *Culex tritaeniorhynchus,*
Chironomidae (midges),
Muscidae such as *Musca domestica* (house fly) and *Muscina stabulans,* Calliphorbae (blow fries), Sarcophagidae (fleshflies),
Anthomyiidae such as *Delia Platura* and *Delia antigua,*
Trypetidae (fruit flies), Drosophilidae (wine flies),
Psychodidae (moth flies), *Tabanidae* (deer flies),
Simuliidae (black flies), Stomoxyinae, etc.;
Coleoptera (beetles):
Diabrotica (corn rootworms) such as *Diacrotica virgilera* and *Diabrotica undecimpunctata,*
Scarabaeidae such as *Anomala cuprea* and *Anomala rufocuprea,* Curculionidae (snout beetles) such as *Lissorphoptrus oryzophilus, Hypera pastica,* and *Calosobruchys chinensis, Neatus ventralis* (darkling beetles) such as *Tenebrio molitor* and *Tribolium castaneum,*
Chrysomelidae (leaf beetles) such as *Aulacophora femoralis* and *Phyllotreta striolata,*
Anobiidae (death-watch beetles),
*Epilachna* spp. such as *Henosepilachna vigintioctopunctata,* Lyctidae (powder-post beetles), Bostrychidae (lesser grain boreres), *Paederus fuscipes,* etc.;
Blattaria (cockroaches):
*Blattella germanica* (croton bugs), *Periplaneta fuliginosa, Peripllaneta americana, Periplaneta brunnea,* etc.;
Thysanoptera (thrips):
*Thrips palmi, Thrips tabaci, Thrips hawaiiensis,* etc.;
Hymenoptera:
Formicidae (ants), Nespa (hornets), Bethylidae (bethylidwasps), Tebthredinodae (sawflies), such as *Athalia rosae japonensis* (cabbage sawfly), etc.;
Orthoptera:
Gryllotalpha (mole crickets), Acridoidea (grasshoppers), etc.;
Siphonaptera (fleas):
*Purex irritans,* etc.;
Anoplura (sucking louses):
*Pediculus humanus capitis, Phthirus pubis,* etc.;
Isoptera (termites):
*Reticulitermes speratus, Coptotermes formosanus,* etc.;
Mites:
Plant parastic Tetranychidae (spider mites) such as *Tetranychus urticae, Panonychus citri, Tetranychus cinnabarinus* and *Panonychus ulmi,*

Animal parastic Ixodidae (ticks) such as Boophilus microphus, House dust mites, etc.

Further, the dithiocarbonimide derivative of the present invention is also useful for noxious insects having resistance against conventional insecticides.

The present invention will be further illustrated by way of the following production examples, formulation examples and biological test examples, all of which are, however, not to be construed to limit the scope thereof.

First, the following will describe typical examples of the production of the dithiocarbonimide derivative of the present invention.

EXAMPLE 1

N-(4-ethoxyphenyl)-S-methyl-S-(2-(α-methoxyimino-α-methoxycarbonylmethyl)phenylmethyl)dithiocarbonimide (1.0 g, 2 mmol) was dissolved in methanol (5 ml), and 40% (w/w) methylamine in methanol (4 ml) was added to the resulting solution and the mixture was reacted at room temperature for 2 hours. The reaction product was concentrated under reduced pressure to give an oily product. This oily product was subjected to silica gel column chromatography to give 0.6 g of N-(4-ethoxyphenyl)-S-methyl-S-(2-(α-methoxyimino-α-N'-methylcarbamoylmethyl)phenylmethyl)dithiocarbonimide (compound 26).

EXAMPLE 2

N-(6-(2,2,2-trifluoroethoxy)-pyridin-3-yl)-S-methyl-S-(2-(α-methoxy-imino-α-methoxycarbonylmethyl)phenylmethyl)dithiocarbonimide (1.0 g, 2 mmol) was dissolved in methanol (5 ml), and 40% (w/w) methylamine in methanol (4 ml) was added to the resulting solution and the mixture was reacted at room temperature for 2 hours. The reaction product was concentrated under reduced pressure to give a solid product. This solid product was recrystallized from ethyl acetate/diethyl ether to give 0.8 g of N-(6-(2,2,2-trifluoroethoxy)-pyridin-3-yl)-S-methyl-S-(2-(α-methoxy-imino-α-N'-methylcarbamoylmethyl)phenylmethyl) dithiocarbonimide (compound 79).

Example 3

N-(4-methoxyphenyl)-S-methyl-S-(2-(α- methoxyimino-α-methoxycarbonylmethyl)phenyl-methyl)dithiocarbonimide (1.0 g, 2 mmol) was dissolved in methanol (5 ml), and 40% (w/w)methylamine in methanol (4 ml) was added to the resulting solution and the mixture was reacted at room temperature for 2 hours. The reaction product was concentrated under reduced pressure to give an oily product. This oily product was subjected to silica gel column chromatography to give 0.6 g of N-(4-methoxyphenyl)-S-methyl-S-(2-(α-methoxyimino-α-N'-methylcarbamoylmethyl)phenylmethyl)dithiocarbonimide (compound 7).

EXAMPLE 4

N-(4-methylphenyl)-S-methyl-S-(2-(α-methoxyimino-α-methoxycarbonylmethyl)phenylmethyl)dithiocarbonimide (1.0 g, 2.5 mmol) was dissolved in methanol (5 ml), and 40% (w/w) methylamine in methanol (4,ml) was added to the resulting solution and reacted at room temperature for 2 hours. The reaction product was concentrated under reduced pressure to give a solid product. This solid product was recrystallized from ethyl acetate/diethyl ether to give 0.8 g of N-(4-methylphenyl)-S-methyl-S-(2-(α-methoxyimino-α-N'-methylcarbamoylmethyl)phenylmethyl) dithiocarbonimide (compound 4).

EXAMPLE 5

N-(3-chlorophenyl)-S-methyl-S-(2-(α-methoxyimino-α-methoxycarbonylmethyl)phenylmethyl)dithiocarbonimide (0.9 g, 2 mmol) was dissolved in methanol (5 ml), and 40% (w/w) methylamine in methanol (4 ml) was added to the resulting solution and the mixture was reacted at room temperature for 2 hours. The reaction product was concentrated under reduced pressure to give an oily product. This oily product was subjected to silica gel column chromatography to give 0.5 g of N-(3-chlorophenyl)-S-meth-S-(2-(α-methoxyimino-α-N'-methylcarbamoylmethyl)phenylmethyl) dithiocarbonimide (compound 9).

EXAMPLE 6

N-phenyl-S-methyl-S-(2-(α-methoxyimino-α-methoxycarbonylmethyl)phenylmethyl)dithiocarbonimide (1.0 g, 2.5 mmol) was dissolved in methanol (5 ml), and 40% (w/w) methylamine in methanol (4 ml) was added to the resulting solution and the mixture was reacted at room temperature for 2 hours. The reaction product was concentrated under reduced pressure to give a solid product. This solid product was recrystallized from ethyl acetate/diethyl ether to give 0.8 g of N-phenyl-S-methyl-S-(2-(α-methoxyimino-α-N'-methylcarbamoylmethyl)phenylmethyl)dithiocarbonimide (compound 1).

EXAMPLE 7

To a solution of S-methyl-N-(3,3-dimethylbutyl)dithiocarbamate (4.2 g, 22 mmol) in N,N-dimethylformamide (50 ml), sodium hydride (0.8 g, 20 mmol, 60% oil dispersion) was added and the resultant mixture was reacted at room temperature for 15 min. Then (E)-3-methoxy-2-(2-bromomethylphenyl)propenoic acid methyl ester (5.7 g, 20 mmol) was added to the reaction solution, and allowed to react for 1 hour at room temperature. Water was added to the reaction mixture, and the product was extracted with ethyl acetate. The obtained organic layer was dried over anhydrous magnesium sulfate. Then the filtered solution was evaporated to give a residue, which was subjected to silica gel column chromatography (6:1 hexane/ethyl acetate) to give 3.5 g (8.7 mmol) of N-(3,3-dimethylbutyl)-S-methyl-S-(2-(α-methoxymethylene-αmethoxycarbonylmethyl)phenylmethyl) dithiocarbonimide (compound 797).

EXAMPLE 8

To a solution of S-methyl-N-(3,3-dimethylbutyl)dithiocarbamate (4.2 g, 22 mmol) in N,N-dimethylformamide (50 ml), sodium hydride (0.8 g, 20 mmol, 60% oil dispersion) was added and the resultant mixture was reacted at room temperature for 15 min. Then (E)-N-methylo2-(2-bromomethylphenyl)-2-methoxyiminoacetamide (5.7 g, 20 mmol) was added to the reaction solution, and allowed to react for 1 hour at room temperature. Water was added to the reaction mixture, and the product was extracted with ether. The obtained organic layer was dried over anhydrous magnesium sulfate. Then the filtered solution was evaporated to give a residue, which was subjected to silica gel column chromatography (2:1 hexane/ethyl acetate) to give 2.1 g (5.3 mmol) of N-(3,3-di-methylbutyl)-S-methyl-S-(2-(α-methoxyimino-α-N'-methylcarbamoylmethyl)phenylmethyl) dithiocarbonimide (compound 431 ).

EXAMPLE 9

To a solution of S-methyl-N-(3,3-dimethylbutyl)dithiocarbamate (4.2 g, 22 mmol) in THF (20 ml), sodium hydride (0.8 g, 20 mmol, 60% oil dispersion) was added and the resultant mixture was reacted at room temperature for 15 min. Then methyl (E)-2-(2bromomethylphenyl)-2-methoxyiminoacetate (5.7 g, 20 mmol) was added to the reaction solution, and allowed to react for 1 hour at room temperature. Water was added to the reaction mixture, and the product was extracted with diethyl ether. The obtained organic layer was dried over anhydrous magnesium sulfate. Then the filtered solution was evaporated to give a residue, which was subjected to silica gel column chromatography (5:1 hexane/ethyl acetate) to give 6.7 g (17 mmol) of N-(3,3-dimethylbutyl)-S-methyl-S-(2-($\alpha$-methoxyimino-$\alpha$-methoxycarbonylmethyl)phenylmethyl)dithiocarbonimide (compound 798).

EXAMPLE 10

To a solution of S-methyl-N-(2-phenylethyl)dithiocarbamate(2.0 g, 9.5 mmol) in THF (30 ml), sodium hydride (0.3 g, 9.5 mmol, 60% oil dispersion) was added and the resultant mixture was reacted at room temperature for 15 min. Then methyl (E)-2-(2-bromomethylphenyl)-2-methoxyiminoacetate (2.4 g, 8.4 mmol) was added to the reaction solution, and allowed to react for 1 hour at room temperature. Water was added to the reaction mixture, and the product was extracted with diethyl ether. The obtained organic layer was dried over anhydrous magnesium sulfate. Then the filtered solution was evaporated to give a residue, which was subjected to silica gel column chromatography (5:1 hexane/ethyl acetate)to give 2.8 g (6.7 mmol) of N-(2-phenylethy)-S-methyl-S-(2-($\alpha$-methoxyimino-$\alpha$-methoxycarbonyhmethyl)phenylmethyl)dithiocarbonimide (compound 800).

EXAMPLE 11

To a solution of N-(2ophenylethyl)-S-methyl-S-(2-($\alpha$-methoxyimino-$\alpha$-methoxylcarbonyhnethyl)phenylethyl)dithiocarbonimide (2.6 g, 6.3 mmol) in methanol (30 ml), a solution of methylaniline in methanol (40%, 5 ml) was added and the resultant mixture was reacted at room temperature for 3 hours. Then the reaction was evaporated to give a residue, which was subjected to silica gel column chromatography (2:1 hexane/ethyl acetate) to give 1.8 g (4.3 mmol) of N-(2-phenylethyl)-S-methyl-S-(2-($\alpha$-methoxyimino-$\alpha$-N'-methylcarbamoylmethyl)phenylmethyl)dithiocarbonimide (compound 475).

EXAMPLE 12

To a solution of S-methyl-N-(2-phenylethyl)dithiocarbamate (2.0 g, 9.5 mmol) in THF (30 ml), sodium hydride (0.3 g, 9.5 mmol, 60% oil dispersion) was added and the resultant mixture was reacted at room temperature for 15 min. Then methyl (E)-3-methoxy-2-(2-bromomethylphenyl) propenoate (2.9 g, 10 mmol) was added to the reaction solution, and allowed to react for 1 hour at room temperature. Water was added to the reaction mixture, and the product was extracted with diethyl ether. The obtained organic layer was dried over anhydrous magnesium sulfate. Then the filtered solution was evaporated to give a residue, which was subjected to silica gel column chromatography (5: 1 hexane/ethyl acetate)to give 3.5 g (8.4 mmol) of N-(2-phenylethyl)-S-methyl-S-(2-($\alpha$-methoxymethylene-$\alpha$-methoxycarbonylmethyl)phenylmethyl)dithiocarbonimide (compound 799).

EXAMPLE 13

To a solution of S-methyl-N-(3-methylbutyl)dithiocarbamate (1.7 g, 9.6 mmol) in THF (30 ml), sodium hydride (0.4 g, 10 mmol, 60% oil dispersion) was added and the resultant mixture was reacted at room temperature for 15 min. Then methyl (E)-3-methoxy-2-(2-bromomethylphenyl) propenoate (2.9 g, 10 mmol) was added to the reaction solution, and allowed to react for 1 hour at room temperature. Water was added to the reaction mixture, and the product was extracted with ethyl acetate. The obtained organic layer was dried over anhydrous magnesium sulfate. Then the filtered solution was evaporated to give a residue, which was subjected to silica gel column chromatography (5: 1 hexane/ethyl acetate) to give 3.5 g (9.2 mmol) of N-(3methylbutyl)-S-methyl-S-(2-($\alpha$-methoxymethylene-$\alpha$-methoxycarbonylinethyl)phenylmethyl)dithiocarbonimide (compound 795).

EXAMPLE 14

To a solution of S-methyl-N-(3-methylbutyl)dithiocarbamate (1.7 g, 9.6 mmol) in THF (30 ml), sodium hydride (0.4 g, 10 mmol, 60% oil dispersion) was added and the resultant mixture was reacted at room temperature for 15 min. Then methyl (E)-2-(2-bromomethylphenyl)-2-methoxyimonoacetate (2.9 g, 10 mmol) was added to the reaction solution, and allowed to react for 1 hour at room temperature. Water was added to the reaction mixture, and the product was extracted with diethyl ether. The obtained organic layer was dried over anhydrous magnesium sulfate. Then the filtered solution was evaporated to give a residue, which was subjected to silica gel column chromatography (5:1 hexane/ethyl acetate) to give 3.4 g (8.9 mmol) of N-(3-methylbutyl)-S-methyl-S-(2-($\alpha$-methoxyimino-$\alpha$-methoxycarbonylmethyl)phenylmethyl)dithiocarbonimide (compound 796).

EXAMPLE 15

To a solution of N-(3-methylbutyl)-S-methyl-S-(2-(ecmethoxyimino-$\alpha$-methoxycarbonylmethyl)phenylmethyl)dithiocarbonimide (1.0 g, 2.6 mmol) in methanol (10 ml), a solution of methylamine in methanol (40%, 5 ml) was added and the resultant mixture was reacted at room temperature for 3 hours. Then the reaction solution was evaporated to give a residue, which was subjected to silica gel column chromatography (2:1 hexane/ethyl acetate) to give 0.6 g (1.6 mmol) of N-(3-methylbutyl)-S-methyl-S-(2-($\alpha$-methoxyimino-$\alpha$-N'-methylcarbamoylmethyl)phenylmethyl)dithiocarbonimide (compound 428).

EXAMPLE 16

To a solution of N-(4-ethoxyphenyl)-S-(2-($\alpha$-methoxymethylene-$\alpha$-methoxycarbonyhnethyl)phenylmethyl)dithiocarbamate (2.1 g, 5 mmol) in DMF (10 ml), anhydrous potassium carbonate (0.83 g, 6 mmol) and then methyl iodide (0.9 g, 6 mmol) were added and the resultant mixture was reacted at room temperature for 2 hours. Then the reaction solution was poured into ice-water and the product was extracted with ethyl acetate. The obtained organic layer was dried over anhydrous magnesium sulfate. Then the filtered solution was evaporated to give a residue, which was subjected to silica gel column chromatography to give 2.0 g of N-(4-ethoxyphenyl)-S-methyl-S-(2-($\alpha$-methoxy-methylene-α-methoxycarbonylmethyl)phenyl-methyl)dithiocarbonimide (compound 845).

Next, typical examples of the dithiocarbonimide derivative of the present invention are shown with their compound numbers in Tables 1 and 2.

TABLE 1

A—N(=SB)(SCH₂—)— phenyl ring with CH₃O—N=C(CONHCH₃)—

| Compound No. | A | B |
|---|---|---|
| 1 | phenyl | methyl |
| 2 | 2-methylphenyl | methyl |
| 3 | 3-methylphenyl | methyl |
| 4 | 4-methylphenyl | methyl |
| 5 | 2-methoxyphenyl | methyl |
| 6 | 3-methoxyphenyl | methyl |
| 7 | 4-methoxyphenyl | methyl |
| 8 | 2-chlorophenyl | methyl |
| 9 | 3-chlorophenyl | methyl |
| 10 | 4-chlorophenyl | methyl |
| 11 | 2-fluorophenyl | methyl |
| 12 | 3-fluorophenyl | methyl |
| 13 | 4-fluorophenyl | methyl |
| 14 | 4-tert-butylphenyl | methyl |
| 15 | 3-bromophenyl | methyl |
| 16 | 4-bromophenyl | methyl |
| 17 | 2-ethylphenyl | methyl |
| 18 | 3-ethylphenyl | methyl |
| 19 | 4-ethylphenyl | methyl |
| 20 | 2-n-propylphenyl | methyl |
| 21 | 4-n-propylphenyl | methyl |
| 22 | 4-isopropylphenyl | methyl |
| 23 | 4-n-butylphenyl | methyl |
| 24 | 2-ethoxyphenyl | methyl |
| 25 | 3-ethoxyphenyl | methyl |
| 26 | 4-ethoxyphenyl | methyl |
| 27 | 3-n-propyloxyphenyl | methyl |
| 28 | 4-n-propyloxyphenyl | methyl |
| 29 | 4-isopropyloxyphenyl | methyl |
| 30 | 4-n-butyloxyphenyl | methyl |
| 31 | 4-phenoxyphenyl | methyl |
| 32 | 3-methylthiophenyl | methyl |
| 33 | 4-methylthiophenyl | methyl |
| 34 | 2-ethylthiophenyl | methyl |
| 35 | 3-ethylthiophenyl | methyl |
| 36 | 4-ethylthiophenyl | methyl |
| 37 | 4-n-propylthiophenyl | methyl |
| 38 | 3-n-butylthiophenyl | methyl |
| 39 | 4-methoxycarbonylphenyl | methyl |
| 40 | 2-cyanophenyl | methyl |
| 41 | 3-cyanophenyl | methyl |
| 42 | 4-cyanophenyl | methyl |
| 43 | 4-nitrophenyl | methyl |
| 44 | 3-nitrophenyl | methyl |
| 45 | 3,4-difluoromethylenedioxyphenyl | methyl |
| 46 | 2-trifluoromethylphenyl | methyl |
| 47 | 3-trifluoromethylphenyl | methyl |
| 48 | 4-trifluoromethylphenyl | methyl |
| 49 | 3-trifluoromethoxyphenyl | methyl |
| 50 | 4-trifluoromethoxyphenyl | methyl |
| 51 | 2,5-dimethylphenyl | methyl |
| 52 | 3,5-dimethylphenyl | methyl |
| 53 | 3,4-dimethylphenyl | methyl |
| 54 | 3,5-dimethoxyphenyl | methyl |
| 55 | 3,4-dimethoxyphenyl | methyl |
| 56 | 2,4-dichlorophenyl | methyl |
| 57 | 3,4-dichlorophenyl | methyl |
| 58 | 3,5-dichlorophenyl | methyl |
| 59 | 3,4-methylenedioxyphenyl | methyl |

TABLE 1-continued

| Compound No. | A | B |
|---|---|---|
| 60 | 3,4,5-trichlorophenyl | methyl |
| 61 | 3,4,5-trimethoxyphenyl | methyl |
| 62 | 3-chloro-4-methylphenyl | methyl |
| 63 | 2-pyridyl | methyl |
| 64 | 3-pyridyl | methyl |
| 65 | 4-pyridyl | methyl |
| 66 | pyridazine-3-yl | methyl |
| 67 | 4,6-dimethylpyrimidin-2-yl | methyl |
| 68 | thiazol-2-yl | methyl |
| 69 | 3-methylisothiazol-5-yl | methyl |
| 70 | 1,3,4-thiadiazol-2-yl | methyl |
| 71 | 4-methylpyrimidin-2-yl | methyl |
| 72 | 5-methylpyrimidin | methyl |
| 73 | 2-methoxypyridin-3-yl | methyl |
| 74 | 2-methoxypyridin-5-yl | methyl |
| 75 | 5-chloropyridin-3-yl | methyl |
| 76 | 5-chloropyridin-2-yl | methyl |
| 77 | 2-ethoxypyridin-5-yl | methyl |
| 78 | 5-isopropyloxypyridin-2-yl | methyl |
| 79 | 2-(2,2,2-trifluoroethoxy)pyridin-5-yl | methyl |
| 80 | 2-chloropyridin-5-yl | methyl |
| 81 | 1,3-dimethylpyrazol-5-yl | methyl |
| 82 | 4,5-dimethylthiazol-2-yl | methyl |
| 83 | phenyl | ethyl |
| 84 | 2-methylphenyl | ethyl |
| 85 | 3-methylphenyl | ethyl |
| 86 | 4-methylphenyl | ethyl |
| 87 | 2-methoxyphenyl | ethyl |
| 88 | 3-methoxyphenyl | ethyl |
| 89 | 4-methoxyphenyl | ethyl |
| 90 | 2-chlorophenyl | ethyl |
| 91 | 3-chlorophenyl | ethyl |
| 92 | 4-chlorophenyl | ethyl |
| 93 | 2-fluorophenyl | ethyl |
| 94 | 3-fluorophenyl | ethyl |
| 95 | 4-fluorophenyl | ethyl |
| 96 | 4-tert-butylphenyl | ethyl |
| 97 | 3-bromophenyl | ethyl |
| 98 | 4-bromophenyl | ethyl |
| 99 | 2-ethylphenyl | ethyl |
| 100 | 3-ethylphenyl | ethyl |
| 101 | 4-ethylphenyl | ethyl |
| 102 | 2-n-propylphenyl | ethyl |
| 103 | 4-n-propylphenyl | ethyl |
| 104 | 4-isopropylphenyl | ethyl |
| 105 | 4-n-butylphenyl | ethyl |
| 106 | 2-ethoxyphenyl | ethyl |
| 107 | 3-ethoxyphenyl | ethyl |
| 108 | 4-ethoxyphenyl | ethyl |
| 109 | 3-n-propyloxyphenyl | ethyl |
| 110 | 4-n-propyloxyphenyl | ethyl |
| 111 | 4-isopropyloxyphenyl | ethyl |
| 112 | 4-n-butyloxyphenyl | ethyl |
| 113 | 4-phenoxyphenyl | ethyl |
| 114 | 3-methylthiophenyl | ethyl |
| 115 | 4-methylthiophenyl | ethyl |
| 116 | 2-ethylthiophenyl | ethyl |
| 117 | 3-ethylthiophenyl | ethyl |
| 118 | 4-ethylthiophenyl | ethyl |
| 119 | 4-n-propylthiophenyl | ethyl |
| 120 | 3-n-butylthiophenyl | ethyl |
| 121 | 4-methoxycarbonylphenyl | ethyl |
| 122 | 2-cyanophenyl | ethyl |
| 123 | 3-cyanophenyl | ethyl |
| 124 | 4-cyanophenyl | ethyl |
| 125 | 4-nitrophenyl | ethyl |

TABLE 1-continued

A—N=C(SB)(SCH₂-C₆H₄-)  with CH₃O—N=C(CONHCH₃) ortho substituent

| Compound No. | A | B |
|---|---|---|
| 126 | 3-nitrophenyl | ethyl |
| 127 | 3,4-difluoromethylenedioxyphenyl | ethyl |
| 128 | 2-trifluoromethylphenyl | ethyl |
| 129 | 3-trifluoromethylphenyl | ethyl |
| 130 | 4-trifluoromethylphenyl | ethyl |
| 131 | 3-trifluoromethoxyphenyl | ethyl |
| 132 | 4-trifluoromethoxyphenyl | ethyl |
| 133 | 2,5-dimethylphenyl | ethyl |
| 134 | 3,5-dimethylphenyl | ethyl |
| 135 | 3,4-dimethylphenyl | ethyl |
| 136 | 3,5-dimethoxyphenyl | ethyl |
| 137 | 3,4-dimethoxyphenyl | ethyl |
| 138 | 2,4-dichlorophenyl | ethyl |
| 139 | 3,4-dichlorophenyl | ethyl |
| 140 | 3,5-dichlorophenyl | ethyl |
| 141 | 3,4-methylenedioxyphenyl | ethyl |
| 142 | 3,4,5-trichlorophenyl | ethyl |
| 143 | 3,4,5-trimethoxyphenyl | ethyl |
| 144 | 3-chloro-4-methylphenyl | ethyl |
| 145 | 2-pyridyl | ethyl |
| 146 | 3-pyridyl | ethyl |
| 147 | 4-pyridyl | ethyl |
| 148 | pyridazin-3-yl | ethyl |
| 149 | 4,6-dimethylpyrimidin-2-yl | ethyl |
| 150 | thiazol-2-yl | ethyl |
| 151 | 3-methylisothiazol-5-yl | ethyl |
| 152 | 1,3,4-thiazolone-2-yl | ethyl |
| 153 | 4-methylpyrimidin-2-yl | ethyl |
| 154 | 5-methylpyrimidin-2-yl | ethyl |
| 155 | 2-methoxypyridin-3-yl | ethyl |
| 156 | 2-methoxypyridin-5-yl | ethyl |
| 157 | 5-chloropyridin-3-yl | ethyl |
| 158 | 5-chlorpyridin-2-yl | ethyl |
| 159 | 2-ethoxypyridin-5-yl | ethyl |
| 160 | 5-isopropyloxypyridin-2-yl | ethyl |
| 161 | 2-(2,2,2-trifluoroethoxy)pyridin-5-yl | ethyl |
| 162 | 2-chloropyridin-5-yl | ethyl |
| 163 | 1,3-dimethylpyrazol-5-yl | ethyl |
| 164 | 4,5-dimethylthiazol-2-yl | ethyl |
| 165 | phenyl | n-propyl |
| 166 | 2-methylphenyl | n-propyl |
| 167 | 3-methylphenyl | n-propyl |
| 168 | 4-methylphenyl | n-propyl |
| 169 | 2-methoxyphenyl | n-propyl |
| 170 | 3-methoxyphenyl | n-propyl |
| 171 | 4-methoxyphenyl | n-propyl |
| 172 | 2-chlorophenyl | n-propyl |
| 173 | 3-chlorophenyl | n-propyl |
| 174 | 4-chlorophenyl | n-propyl |
| 175 | 2-fluorophenyl | n-propyl |
| 176 | 3-fluorophenyl | n-propyl |
| 177 | 4-fluorophenyl | n-propyl |
| 178 | 4-tert-butylphenyl | n-propyl |
| 179 | 3-bromophenyl | n-propyl |
| 180 | 4-bromophenyl | n-propyl |
| 181 | 2-ethylphenyl | n-propyl |
| 182 | 3-ethylphenyl | n-propyl |
| 183 | 4-ethylphenyl | n-propyl |
| 184 | 2-n-propylphenyl | n-propyl |
| 185 | 4-n-propylphenyl | n-propyl |
| 186 | 4-isopropylphenyl | n-propyl |
| 187 | 4-n-butylphenyl | n-propyl |
| 188 | 2-ethoxyphenyl | n-propyl |
| 189 | 3-ethoxyphenyl | n-propyl |
| 190 | 4-ethoxyphenyl | n-propyl |
| 191 | 3-n-propyloxyphenyl | n-propyl |
| 192 | 4-n-propyloxyphenyl | n-propyl |
| 193 | 4-isopropyloxyphenyl | n-propyl |
| 194 | 4-n-butyloxyphenyl | n-propyl |
| 195 | 4-phenoxyphenyl | n-propyl |
| 196 | 3-methylthiophenyl | n-propyl |
| 197 | 4-methylthiophenyl | n-propyl |
| 198 | 2-ethylthiophenyl | n-propyl |
| 199 | 3-ethylthiophenyl | n-propyl |
| 200 | 4-ethylthiophenyl | n-propyl |
| 201 | 4-n-propylthiophenyl | n-propyl |
| 202 | 3-n-butylthiophenyl | n-propyl |
| 203 | 4-methoxycarbonylphenyl | n-propyl |
| 204 | 2-cyanophenyl | n-propyl |
| 205 | 3-cyanophenyl | n-propyl |
| 206 | 4-cyanophenyl | n-propyl |
| 207 | 4-nitrophenyl | n-propyl |
| 208 | 3-nitrophenyl | n-propyl |
| 209 | 3,4-difluoromethylenedioxyphenyl | n-propyl |
| 210 | 2-trifluoromethylphenyl | n-propyl |
| 211 | 3-trifluoromethylphenyl | n-propyl |
| 212 | 4-trifluoromethylphenyl | n-propyl |
| 213 | 3-trifluoromethoxyphenyl | n-propyl |
| 214 | 4-trifluoromethoxyphenyl | n-propyl |
| 215 | 2,5-dimethylphenyl | n-propyl |
| 216 | 3,5-dimethylphenyl | n-propyl |
| 217 | 3,4-dimethylphenyl | n-propyl |
| 218 | 3,5-dimethoxyphenyl | n-propyl |
| 219 | 3,4-dimethoxyphenyl | n-propyl |
| 220 | 2,4-dichlorophenyl | n-propyl |
| 221 | 3,4-dichlorophenyl | n-propyl |
| 222 | 3,5-dichlorophenyl | n-propyl |
| 223 | 3,4-methylenedioxyphenyl | n-propyl |
| 224 | 3,4,5-trichlorophenyl | n-propyl |
| 225 | 3,4,5-trimethoxyphenyl | n-propyl |
| 226 | 3-chloro-4-methylphenyl | n-propyl |
| 227 | 2-pyridyl | n-propyl |
| 228 | 3-pyridyl | n-propyl |
| 229 | 4-pyridyl | n-propyl |
| 230 | pyridazin-3-yl | n-propyl |
| 231 | 14,6-dimethylpyrimidin-2-yl | n-propyl |
| 232 | thiazol-2-yl | n-propyl |
| 233 | 3-methylisothiazol-5-yl | n-propyl |
| 234 | 1,3,4-thiazolon-2-yl | n-propyl |
| 235 | 4-methylpyrimidin-2-yl | n-propyl |
| 236 | 5-methylpyrimidin-2-yl | n-propyl |
| 237 | 2-methoxypyridin-3-yl | n-propyl |
| 238 | 2-methoxypyridin-5-yl | n-propyl |
| 239 | 5-chloropyridin-3-yl | n-propyl |
| 240 | 5-chlorpyridin-2-yl | n-propyl |
| 241 | 2-ethoxypyridin-5-yl | n-propyl |
| 242 | 5-isopropyloxypyridin-2-yl | n-propyl |
| 243 | 2-(2,2,2-trifluoroethoxy)pyridin-5-yl | n-propyl |
| 244 | 2-chloropyridin-5-yl | n-propyl |
| 245 | 1,3-dimethylpyrazol-5-yl | n-propyl |
| 246 | 4,5-dimethylthiazol-2-yl | n-propyl |
| 247 | phenyl | isopropyl |
| 248 | 2-methylphenyl | isopropyl |
| 249 | 3-methylphenyl | isopropyl |
| 250 | 4-methylphenyl | isopropyl |
| 251 | 2-methoxyphenyl | isopropyl |
| 252 | 3-methoxyphenyl | isopropyl |
| 253 | 4-methoxyphenyl | isopropyl |
| 254 | 2-chlorophenyl | isopropyl |
| 255 | 3-chlorophenyl | isopropyl |
| 256 | 4-chlorophenyl | isopropyl |
| 257 | 2-fluorophenyl | isopropyl |
| 258 | 3-fluorophenyl | isopropyl |
| 259 | 4-fluorophenyl | isopropyl |

TABLE 1-continued

A—N(SB)(SCH₂-C₆H₄-)... CH₃O—N, CONHCH₃

| Compound No. | A | B |
|---|---|---|
| 260 | 4-tert-butylphenyl | isopropyl |
| 261 | 3-bromophenyl | isopropyl |
| 262 | 4-bromophenyl | isopropyl |
| 263 | 2-ethylphenyl | isopropyl |
| 264 | 3-ethylphenyl | isopropyl |
| 265 | 4-ethylphenyl | isopropyl |
| 266 | 2-n-propylphenyl | isopropyl |
| 267 | 4-n-propylphenyl | isopropyl |
| 268 | 4-isopropylphenyl | isopropyl |
| 269 | 4-n-butylphenyl | isopropyl |
| 270 | 2-ethoxyphenyl | isopropyl |
| 271 | 3-ethoxyphenyl | isopropyl |
| 272 | 4-ethoxyphenyl | isopropyl |
| 273 | 3-n-propyloxyphenyl | isopropyl |
| 274 | 4-n-propyloxyphenyl | isopropyl |
| 275 | 4-isopropyloxyphenyl | isopropyl |
| 276 | 4-n-butyloxyphenyl | isopropyl |
| 277 | 4-phenoxyphenyl | isopropyl |
| 278 | 3-methylthiophenyl | isopropyl |
| 279 | 4-methylthiophenyl | isopropyl |
| 280 | 2-ethylthiophenyl | isopropyl |
| 281 | 3-ethylthiophenyl | isopropyl |
| 282 | 4-ethylthiophenyl | isopropyl |
| 283 | 4-n-propylthiophenyl | isopropyl |
| 284 | 3-n-butylthiophenyl | isopropyl |
| 285 | 4-methoxycarbonylphenyl | isopropyl |
| 286 | 2-cyanophenyl | isopropyl |
| 287 | 3-cyanophenyl | isopropyl |
| 288 | 4-cyanophenyl | isopropyl |
| 289 | 4-nitrophenyl | isopropyl |
| 290 | 3-nitrophenyl | isopropyl |
| 291 | 3,4-difluoromethylenedioxyphenyl | isopropyl |
| 292 | 2-trifluoromethylphenyl | isopropyl |
| 293 | 3-trifluoromethylphenyl | isopropyl |
| 294 | 4-trifluoromethylphenyl | isopropyl |
| 295 | 3-trifluoromethoxyphenyl | isopropyl |
| 296 | 4-trifluoromethoxyphenyl | isopropyl |
| 297 | 2,5-dimethylphenyl | isopropyl |
| 298 | 3,5-dimethylphenyl | isopropyl |
| 299 | 3,4-dimethylphenyl | isopropyl |
| 300 | 3,5-dimethoxyphenyl | isopropyl |
| 301 | 3,4-dimethoxyphenyl | isopropyl |
| 302 | 2,4-dichlorophenyl | isopropyl |
| 303 | 3,4-dichlorophenyl | isopropyl |
| 304 | 3,5-dichlorophenyl | isopropyl |
| 305 | 3,4-methylenedioxyphenyl | isopropyl |
| 306 | 3,4,5-trichlorophenyl | isopropyl |
| 307 | 3,4,5-trimethoxyphenyl | isopropyl |
| 308 | 3-chloro-4-methylphenyl | isopropyl |
| 309 | 2-pyridyl | isopropyl |
| 310 | 3-pyridyl | isopropyl |
| 311 | 4-pyridyl | isopropyl |
| 312 | pyridazin-3-yl | isopropyl |
| 313 | 4,6-dimethylpyrimidin-2-yl | isopropyl |
| 314 | thiazol-2-yl | isopropyl |
| 315 | 3-methylisothiazol-5-yl | isopropyl |
| 316 | 1,3,4-thiazolon-2-yl | isopropyl |
| 317 | 4-methylpyrimidin-2-yl | isopropyl |
| 318 | 5-methylpyrimidin-2-yl | isopropyl |
| 319 | 2-methoxypyridin-3-yl | isopropyl |
| 320 | 2-methoxypyridin-5-yl | isopropyl |
| 321 | 5-chloropyridin-3-yl | isopropyl |
| 322 | 5-chlorpyridin-2-yl | isopropyl |
| 323 | 2-ethoxypyridin-5-yl | isopropyl |
| 324 | 5-isopropyloxypyridin-2-yl | isopropyl |
| 325 | 2-(2,2,2-trifluoroethoxy)pyridin-5-yl | isopropyl |
| 326 | 2-chloropyridin-5-yl | isopropyl |
| 327 | 1,3-dimethylpyrazol-5-yl | isopropyl |
| 328 | 4,5-dimethylthiazol-2-yi | isopropyl |
| 329 | phenyl | n-butyl |
| 330 | 2-methylphenyl | n-butyl |
| 331 | 3-methylphenyl | n-butyl |
| 332 | 4-methylphenyl | n-butyl |
| 333 | 2-methoxyphenyl | n-butyl |
| 334 | 3-methoxyphenyl | n-butyl |
| 335 | 4-methoxyphenyl | n-butyl |
| 336 | 2-chlorophenyl | n-butyl |
| 337 | 3-chlorophenyl | n-butyl |
| 338 | 4-chlorophenyl | n-butyl |
| 339 | 2-fluorophenyl | n-butyl |
| 340 | 3-fluorophenyl | n-butyl |
| 341 | 4-fluorophenyl | n-butyl |
| 342 | 4-tert-butylphenyl | n-butyl |
| 343 | 3-bromophenyl | n-butyl |
| 344 | 4-bromophenyl | n-butyl |
| 345 | 2-ethylphenyl | n-butyl |
| 346 | 3-ethylphenyl | n-butyl |
| 347 | 4-ethylphenyl | n-butyl |
| 348 | 2-n-propylphenyl | n-butyl |
| 349 | 4-n-propylphenyl | n-butyl |
| 350 | 4-isopropylphenyl | n-butyl |
| 351 | 4-n-butylphenyl | n-butyl |
| 352 | 2-ethoxyphenyl | n-butyl |
| 353 | 3-ethoxyphenyl | n-butyl |
| 354 | 4-ethoxyphenyl | n-butyl |
| 355 | 3-n-propyloxyphenyl | n-butyl |
| 356 | 4-n-propyloxyphenyl | n-butyl |
| 357 | 4-isopropyloxyphenyl | n-butyl |
| 358 | 4-n-butyloxyphenyl | n-butyl |
| 359 | 4-phenoxyphenyl | n-butyl |
| 360 | 3-methylthiophenyl | n-butyl |
| 361 | 4-methylthiophenyl | n-butyl |
| 362 | 2-ethylthiophenyl | n-butyl |
| 363 | 3-ethylthiophenyl | n-butyl |
| 364 | 4-ethylthiophenyl | n-butyl |
| 365 | 4-n-propylthiophenyl | n-butyl |
| 366 | 3-n-butylthiophenyl | n-butyl |
| 367 | 4-methoxycarbonylphenyl | n-butyl |
| 368 | 2-cyanophenyl | n-butyl |
| 369 | 3-cyanophenyl | n-butyl |
| 370 | 4-cyanophenyl | n-butyl |
| 371 | 4-nitrophenyl | n-butyl |
| 372 | 3-nitrophenyl | n-butyl |
| 373 | 3,4-difluoromethylenedioxyphenyl | n-butyl |
| 374 | 2-trifluoromethylphenyl | n-butyl |
| 375 | 3-trifluoromethylphenyl | n-butyl |
| 376 | 4-trifluoromethylphenyl | n-butyl |
| 377 | 3-trifluoromethoxyphenyl | n-butyl |
| 378 | 4-trifluoromethoxyphenyl | n-butyl |
| 379 | 2,5-dimethylphenyl | n-butyl |
| 380 | 3,5-dimethylphenyl | n-butyl |
| 381 | 3,4-dimethylphenyl | n-butyl |
| 382 | 3,5-dimethoxyphenyl | n-butyl |
| 383 | 3,4-dimethoxyphenyl | n-butyl |
| 384 | 2,4-dichlorophenyl | n-butyl |
| 385 | 3,4-dichlorophenyl | n-butyl |
| 386 | 3,5-dichlorophenyl | n-butyl |
| 387 | 3,4-methylenedioxyphenyl | n-butyl |
| 388 | 3,4,5-trichlorophenyl | n-butyl |
| 389 | 3,4,5-trimethoxyphenyl | n-butyl |
| 390 | 3-chloro-4-methylphenyl | n-butyl |
| 391 | 2-pyridyl | n-butyl |
| 392 | 3-pyridyl | n-butyl |
| 393 | 4-pyridyl | n-butyl |

TABLE 1-continued

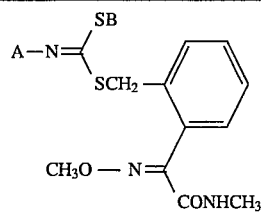

| Compound No. | A | B |
| --- | --- | --- |
| 394 | pyridazin-3-yl | n-butyl |
| 395 | 4,6-dimethylpyrimidin-2-yl | n-butyl |
| 396 | thiazol-2-yl | n-butyl |
| 397 | 3-methylisothiazol-5-yl | n-butyl |
| 398 | 1,3,4-thiazolon-2-yl | n-butyl |
| 399 | 4-methylpyrimidin-2-yl | n-butyl |
| 400 | 5-methylpyrimidin-2-yl | n-butyl |
| 401 | 2-methoxypyridin-3-yl | n-butyl |
| 402 | 2-methoxypyridin-5-yl | n-butyl |
| 403 | 5-chloropyridin-3-yl | n-butyl |
| 404 | 5-chlorpyridin-2-yl | n-butyl |
| 405 | 2-ethoxypyridin-5-yl | n-butyl |
| 406 | 5-isopropyloxypyridin-2-yl | n-butyl |
| 407 | 2-(2,2,2-trifluoroethoxy)pyridin-5-yl | n-butyl |
| 408 | 2-chloropyridin-5-yl | n-butyl |
| 409 | 1,3-dimethylpyrazol-5-yl | n-butyl |
| 410 | 4,5-dimethylthiazol-2-yl | n-butyl |
| 411 | methyl | methyl |
| 412 | ethyl | methyl |
| 413 | propyl | methyl |
| 414 | butyl | methyl |
| 415 | pentyl | methyl |
| 416 | hexyl | methyl |
| 417 | heptyl | methyl |
| 418 | octyl | methyl |
| 419 | nonyl | methyl |
| 420 | decyl | methyl |
| 421 | 1-methylethyl | methyl |
| 422 | 1-methylpropyl | methyl |
| 423 | 2-methylpropyl | methyl |
| 424 | 1,1-dimethylethyl | methyl |
| 425 | 1-methylbutyl | methyl |
| 426 | 1-ethylpropyl | methyl |
| 427 | 2-methylbutyl | methyl |
| 428 | 3-methylbutyl | methyl |
| 429 | 2,3-dimethylbutyl | methyl |
| 430 | 1,3-dimethylbutyl | methyl |
| 431 | 3,3-dimethylbutyl | methyl |
| 432 | 1-methylpentyl | methyl |
| 433 | 1-ethylpentyl | methyl |
| 434 | 1-methylhexyl | methyl |
| 435 | 2-ethylhexyl | methyl |
| 436 | 1,5-dimethylhexyl | methyl |
| 437 | cyclopropyl | methyl |
| 438 | cyclobutyl | methyl |
| 439 | cyclopentyl | methyl |
| 440 | cyclohexyl | methyl |
| 441 | cycloheptyl | methyl |
| 442 | cyclooctyl | methyl |
| 443 | cyclodecyl | methyl |
| 444 | 2-methylcyclohexyl | methyl |
| 445 | 3-methylcyclohexyl | rfiethyl |
| 446 | 4-methylcyclohexyl | methyl |
| 447 | 2,3-dimethylcyclohexyl | methyl |
| 448 | cyclopropylmethyl | methyl |
| 449 | cyclobutylmethyl | methyl |
| 450 | cyclopentylmethyl | methyl |
| 451 | cyclohexylmethyl | methyl |
| 452 | 1-adamantyl | methyl |
| 453 | 2-adamantyl | methyl |
| 454 | 1-adamantylmethyl | methyl |
| 455 | exo-2-norbornyl | methyl |
| 456 | endo-2-norbornyl | methyl |
| 457 | allyl | methyl |
| 458 | 2-methylallyl | methyl |
| 459 | propargyl | methyl |
| 460 | 2-fluoroethyl | methyl |

TABLE 1-continued

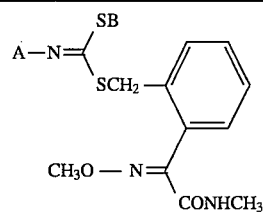

| Compound No. | A | B |
| --- | --- | --- |
| 461 | 2,2,2-trifluoroethyl | methyl |
| 462 | 2-methoxyethyl | methyl |
| 463 | 3-methoxypropyl | methyl |
| 464 | 2-ethoxyethyl | methyl |
| 465 | 3-ethoxypropyl | methyl |
| 466 | 2-methoxy-1-methylethyl | methyl |
| 467 | 3-((1-methyl)ethoxy)propyl | methyl |
| 468 | 3-butoxypropyl | methyl |
| 469 | 2,2-dimethoxyethyl | methyl |
| 470 | 2,2-diethoxyethyl | methyl |
| 471 | 2-ethylthioethyl | methyl |
| 472 | tetrahydrofurfuryl | methyl |
| 473 | 2-cyanoethy | methyl |
| 474 | benzyl | methyl |
| 475 | 2-phenylethyl | methyl |
| 476 | 3-phenylpropyl | methyl |
| 477 | 4-phenylbutyl | methyl |
| 478 | 1-phenylethyl | methyl |
| 479 | 2-phenylpropyl | methyl |
| 480 | 1-methyl-3-phenylpropyl | methyl |
| 481 | 3,3-diphenylpropyl | methyl |
| 482 | 1,2,3,4-tetrahydro-1-naphthyl | methyl |
| 483 | 1-indanyl | methyl |
| 484 | 2-indanyl | methyl |
| 485 | furfuryl | methyl |
| 486 | 2-thiophenmethyl | methyl |
| 487 | 2-methylbenzyl | methyl |
| 488 | 2-trifluoromethylbenzyl | methyl |
| 489 | 2-chlorobenzyl | methyl |
| 490 | 2-bromobenzyl | methyl |
| 491 | 2-methoxybenzyl | methyl |
| 492 | 2-ethoxybenzyl | methyl |
| 493 | 3-methylbenzyl | methyl |
| 494 | 3-trifluoromethylbenzyl | methyl |
| 495 | 3-fluorobenzyl | methyl |
| 496 | 3-chlorobenzyl | methyl |
| 497 | 3-bromobenzyl | methyl |
| 498 | 3-iodobenzyl | methyl |
| 499 | 3-methoxybenzyl | methyl |
| 500 | 3-ethoxybenzyl | methyl |
| 501 | 4-methylbenzyl | methyl |
| 502 | 4-trifluoromethylbenzyl | methyl |
| 503 | 4-fluorobenzyl | methyl |
| 504 | 4-chlorobenzyl | methyl |
| 505 | 4-bromobenzyl | methyl |
| 506 | 4-methoxybenzyl | methyl |
| 507 | 4-trifluoromethoxybenzyl | methyl |
| 508 | 4-ethoxybenzyl | methyl |
| 509 | 2,3-dimethoxybenzyl | methyl |
| 510 | 2,4-dichlorobenzyl | methyl |
| 511 | 2,5-difluorobenzyl | methyl |
| 512 | 2,6-difluorobenzyl | methyl |
| 513 | 3,4-dimethoxybenzyl | methyl |
| 514 | 3,5-bis(trifluoromethyl)benzyl | methyl |
| 516 | piperonyl | methyl |
| 517 | 2-methylphenethyl | imthyl |
| 518 | 2-trifluoromethylphenethyl | methyl |
| 519 | 2-fluorophenethy | methyl |
| 520 | 2-chlorophenethyl | methyl |
| 521 | 2-bromophenethyl | methyl |
| 522 | 2-methoxyphenethyl | methyl |
| 523 | 2-ethoxyphenethyl | methyl |
| 524 | 3-methylphenethyl | methyl |
| 525 | 3-trifluoromethylphenethyl | methyl |
| 526 | 3-fluorophenethyl | methyl |
| 527 | 3-chlorophenethyl | methyl |
| 528 | 3-bromophenethyl | ·methyl |

TABLE 1-continued

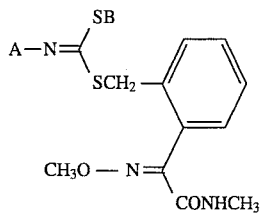

| Compound No. | A | B |
|---|---|---|
| 529 | 3-methoxyphenethyl | methyl |
| 530 | 3-ethoxyphenethyl | methyl |
| 531 | 4-methylphenethyl | methyl |
| 532 | 4-trifluoromethylphenethyl | methyl |
| 533 | 4-fluorophenethyl | methyl |
| 534 | methyl | ethyl |
| 535 | ethyl | ethyl |
| 536 | propyl | ethyl |
| 537 | butyl | ethyl |
| 538 | pentyl | ethyl |
| 539 | hexyl | ethyl |
| 540 | heptyl | ethyl |
| 541 | octyl | ethyl |
| 542 | nonyl | ethyl |
| 543 | decyl | ethyl |
| 544 | 1-methylethyl | ethyl |
| 545 | 1-methylpropyl | ethyl |
| 546 | 2-methylpropyl | ethyl |
| 547 | 1,1-dimethylethyl | ethyl |
| 548 | 1-methylbutyl | ethyl |
| 549 | 1-ethylpropyl | ethyl |
| 550 | 2-methylbutyl | ethyl |
| 551 | 3-methylbutyl | ethyl |
| 552 | 2,3-dimethylbutyl | ethyl |
| 553 | 1,3-dimethylbutyl | ethyl |
| 554 | 3,3-dimethylbutyl | ethyl |
| 555 | 1-methylpentyl | ethyl |
| 556 | 1-ethylpentyl | ethyl |
| 557 | 1-methylhexyl | ethyl |
| 558 | 2-ethylhexyl | ethyl |
| 559 | 1,5-dimethylhexyl | ethyl |
| 560 | cyclopropyl | ethyl |
| 561 | cyclobutyl | ethyl |
| 562 | cyclopentyl | ethyl |
| 563 | cyclohexyl | ethyl |
| 564 | cycloheptyl | ethyl |
| 565 | cyclooctyl | ethyl |
| 566 | cyclodecyl | ethyl |
| 567 | 2-methylcyclohexyl | ethyl |
| 568 | 3-methylcyclohexyl | ethyl |
| 569 | 4-methylcyclohexyl | ethyl |
| 570 | 2,3-dimethylcyclohexyl | ethyl |
| 571 | cyclopropylmethyl | ethyl |
| 572 | cyclobutylmethyl | ethyl |
| 573 | cyclopentylmethyl | ethyl |
| 574 | cyclohexylmethyl | ethyl |
| 575 | 1-adamantyl | ethyl |
| 576 | 2-adamantyl | ethyl |
| 577 | 1-adamantylmethyl | ethyl |
| 578 | exo-2-norbornyl | ethyl |
| 579 | endo-2-norbornyl | ethyl |
| 580 | allyl | ethyl |
| 581 | 2-methylallyl | ethyl |
| 582 | propargyl | ethyl |
| 583 | 2-fluoroethyl | ethyl |
| 584 | 2,2,2-trifluoroethyl | ethyl |
| 585 | 2-methoxyethyl | ethyl |
| 586 | 3-methoxypropyl | ethyl |
| 587 | 2-ethoxyethyl | ethyl |
| 588 | 3-ethoxypropyl | ethyl |
| 589 | 2-methoxy-1-methylethyl | ethyl |
| 590 | 3-((1-methyl)ethoxy)propyl | ethyl |
| 591 | 3-butoxypropyl | ethyl |
| 592 | 2,2-dimethoxyethyl | ethyl |
| 593 | 2,2-diethoxyethyl | ethyl |
| 594 | 2-ethylthioethyl | ethyl |
| 595 | tetrahydrofurfuryl | ethyl |

TABLE 1-continued

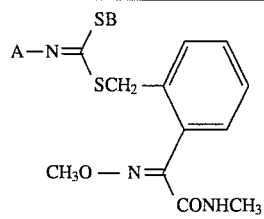

| Compound No. | A | B |
|---|---|---|
| 596 | 2-cyanoethyl | ethyl |
| 597 | benzyl | ethyl |
| 598 | 2-phenylethyl | ethyl |
| 599 | 3-phenylpropyl | ethyl |
| 600 | 4-phenylbutyl | ethyl |
| 601 | 1-phenylethyl | ethyl |
| 602 | 2-phenylpropyl | ethyl |
| 603 | 1-methyl-3-phenylpropyl | ethyl |
| 604 | 3,3-diphenylpropyl | ethyl |
| 605 | 1,2,3,4-tetrahydro-1-naphthyl | ethyl |
| 606 | 1-indanyl | ethyl |
| 607 | 2-indanyl | ethyl |
| 608 | furfuryl | ethyl |
| 609 | 2-thiophenmethyl | ethyl |
| 610 | 2-methybenzyl | ethyl |
| 611 | 2-trifluoromethylbenzyl | ethyl |
| 612 | 2-chlorobenzyl | ethyl |
| 613 | 2-bromobenzyl | ethyl |
| 614 | 2-methoxybenzyl | ethyl |
| 615 | 2-ethoxybenzyl | ethyl |
| 616 | 3-methylbenzyl | ethyl |
| 617 | 3-trifluoromethylbenzyl | ethyl |
| 618 | 3-fluorobenzyl | ethyl |
| 619 | 3-chlorobenzyl | ethyl |
| 620 | 3-bromobenzyl | ethyl |
| 621 | 3-iodobenzyl | ethyl |
| 622 | 3-methoxybenzyl | ethyl |
| 623 | 3-ethoxybenzyl | ethyl |
| 624 | 4-methylbenzyl | ethyl |
| 625 | 4-trifluoromethylbenzyl | ethyl |
| 626 | 4-fluorobenzyl | ethyl |
| 627 | 4-chlorobenzyl | ethyl |
| 628 | 4-bromobenzyl | ethyl |
| 629 | 4-methoxybenzyl | ethyl |
| 630 | 4-trifluoromethoxybenzyl | ethyl |
| 631 | 4-ethoxybenzyl | ethyl |
| 632 | 2,3-dimethoxybenzyl | ethyl |
| 633 | 2,4-dichlorobenzyl | ethyl |
| 634 | 2,5-difluorobenzyl | ethyl |
| 635 | 2,6-difluorobenzyl | ethyl |
| 636 | 3,4-dimethoxybenzyl | ethyl |
| 637 | 3,5-bis(trifluoromethyl)benzyl | ethyl |
| 638 | 2,4,6-trimethoxybenzyl | ethyl |
| 639 | piperonyl | ethyl |
| 640 | 2-methylphenethyl | ethyl |
| 641 | 2-trifluoromethylphenethyl | ethyl |
| 642 | 2-fluorophenethyl | ethyl |
| 643 | 2-chlorophenethyl | ethyl |
| 644 | 2-bromophenethyl | ethyl |
| 645 | 2-methoxyphenethyl | ethyl |
| 646 | 2-ethoxyphenethyl | ethyl |
| 647 | 3-methylphenethyl | ethyl |
| 648 | 3-trifluoromethylphenethyl | ethyl |
| 649 | 3-fluorophenethyl | ethyl |
| 650 | 3-chlorophenethyl | ethyl |
| 651 | 3-bromophenethyl | ethyl |
| 652 | 3-methoxyphenethyl | ethyl |
| 653 | 3-ethoxyphenethyl | ethyl |
| 654 | 4-methylphenethyl | ethyl |
| 655 | 4-trifluoromethylphenethyl | ethyl |
| 656 | 4-fluorophenethyl | ethyl |
| 657 | methyl | isopropyl |
| 658 | ethyl | isopropyl |
| 659 | propyl | isopropyl |
| 660 | butyl | isopropyl |
| 661 | pentyl | isopropyl |
| 662 | hexyl | isopropyl |

TABLE 1-continued $$\text{structure with A-N=C(SB)(SCH}_2\text{-phenyl-C(=N-OCH}_3\text{)CONHCH}_3\text{)}$$

| Compound No. | A | B |
|---|---|---|
| 663 | heptyl | isopropyl |
| 664 | octyl | isopropyl |
| 665 | nonyl | isopropyl |
| 666 | decyl | isopropyl |
| 667 | 1-methylethyl | isopropyl |
| 668 | 1-methylpropyl | isopropyl |
| 669 | 2-methylpropyl | isopropyl |
| 670 | 1,1-dimethylethyl | isopropyl |
| 671 | 1-methylbutyl | isopropyl |
| 672 | 1-ethylpropyl | isopropyl |
| 673 | 2-methylbutyl | isopropyl |
| 674 | 3-methylbutyl | isopropyl |
| 675 | 2,3-dimethylbutyl | isopropyl |
| 676 | 1,3-dimethylbutyl | isopropyl |
| 677 | 3,3-dimethylbutyl | isopropyl |
| 678 | 1-methylpentyl | isopropyl |
| 679 | 1-ethylpentyl | isopropyl |
| 680 | 1-methylhexyl | isopropyl |
| 681 | 2-ethylhexyl | isopropyl |
| 682 | 1,5-dimethylhexyl | isopropyl |
| 683 | cyclopropyl | isopropyl |
| 684 | cyclobutyl | isopropyl |
| 685 | cyclopentyl | isopropyl |
| 686 | cyclohexyl | isopropyl |
| 687 | cycloheptyl | isopropyl |
| 688 | cyclooctyl | isopropyl |
| 689 | cyclodecyl | isopropyl |
| 690 | 2-methylcyclohexyl | isopropyl |
| 691 | 3-methylcyclohexyl | isopropyl |
| 692 | 4-methylcyclohexyl | isopropyl |
| 693 | 2,3-dimethylcyclohexyl | isopropyl |
| 694 | cyclopropylmethyl | isopropyl |
| 695 | cyclobutylmethyl | isopropyl |
| 696 | cyclopentylmethyl | isopropyl |
| 697 | cyclohexylmethyl | isopropyl |
| 698 | 1-adamantyl | isopropyl |
| 699 | 2-adamantyl | isopropyl |
| 700 | 1-adamantylmethyl | isopropyl |
| 701 | exo-2-norbornyl | isopropyl |
| 702 | endo-2-norbornyl | isopropyl |
| 703 | allyl | isopropyl |
| 704 | 2-methylallyl | isopropyl |
| 705 | propargyl | isopropyl |
| 706 | 2-fluoroethyl | isopropyl |
| 707 | 2,2,2-trifluoroethyl | isopropyl |
| 708 | 2-methoxyethyl | isopropyl |
| 709 | 3-methoxypropyl | isopropyl |
| 710 | 2-ethoxyethyl | isopropyl |
| 711 | 3-ethoxypropyl | isopropyl |
| 712 | 2-methoxy-1-methylethyl | isopropyl |
| 713 | 3-((1-methyl)ethoxy)propyl | isopropyl |
| 714 | 3-butoxypropyl | isopropyl |
| 715 | 2,2-dimethoxyethyl | isopropyl |
| 716 | 2,2-diethoxyethyl | isopropyl |
| 717 | 2-ethylthioethyl | isopropyl |
| 718 | tetrahydrofurfuryl | isopropyl |
| 719 | 2-cyanoethyl | isopropyl |
| 720 | benzyl | isopropyl |
| 721 | 2-phenylethyl | isopropyl |
| 722 | 3-phenylpropyl | isopropyl |
| 723 | 4-phenylbutyl | isopropyl |
| 724 | 1-phenylethyl | isopropyl |
| 725 | 2-phenylpropyl | isopropyl |
| 726 | 1-methyl-3-phenylpropyl | isopropyl |
| 727 | 3,3-diphenylpropyl | isopropyl |
| 728 | 1,2,3,4-tetrahydro-1-naphthyl | isopropyl |
| 729 | 1-indanyl | isopropyl |
| 730 | 2-indanyl | isopropyl |
| 731 | furfuryl | isopropyl |
| 732 | 2-thiophenmethyl | isopropyl |
| 733 | 2-methylbenzyl | isopropyl |
| 734 | 2-trifluoromethylbenzyl | isopropyl |
| 735 | 2-chlorobenzyl | isopropyl |
| 736 | 2-bromobenzyl | isopropyl |
| 737 | 2-methoxybenzyl | isopropyl |
| 738 | 2-ethoxybenzyl | isopropyl |
| 739 | 3-methylbenzyl | isopropyl |
| 740 | 3-trifluoromethylbenzyl | isopropyl |
| 741 | 3-fluorobenzyl | isopropyl |
| 742 | 3-chlorobenzyl | isopropyl |
| 743 | 3-bromobenzyl | isopropyl |
| 744 | 3-iodobenzyl | isopropyl |
| 745 | 3-methoxybenzyl | isopropyl |
| 746 | 3-ethoxybenzyl | isopropyl |
| 747 | 4-methylbenzyl | isopropyl |
| 748 | 4-trifluoromethylbenzyl | isopropyl |
| 749 | 4-fluorobenzyl | isopropyl |
| 750 | 4-chlorobenzyl | isopropyl |
| 751 | 4-bromobenzyl | isopropyl |
| 752 | 4-methoxybenzyl | isopropyl |
| 753 | 4-trifluoromethoxybenzyl | isopropyl |
| 754 | 4-ethoxybenzyl | isopropyl |
| 755 | 2,3-dimethoxybenzyl | isopropyl |
| 756 | 2,4-dichlorobenzyl | isopropyl |
| 757 | 2,5-difluorobenzyl | isopropyl |
| 758 | 2,6-difluorobenzyl | isopropyl |
| 759 | 3,4-dimethoxybenzyl | isopropyl |
| 760 | 3,5-bis(trifluoromethyl)benzyl | isopropyl |
| 761 | 2,4,6-trimethoxybenzyl | isopropyl |
| 762 | piperonyl | isopropyl |
| 763 | 2-methylphenethyl | isopropyl |
| 764 | 2-trifluoromethylphenethyl | isopropyl |
| 765 | 2-fluorophenethyl | isopropyl |
| 766 | 2-chlorophenethyl | isopropyl |
| 767 | 2-bromophenethyl | isopropyl |
| 768 | 2-methoxyphenethyl | isopropyl |
| 769 | 2-ethoxyphenethyl | isopropyl |
| 770 | 3-methylphenethyl | isopropyl |
| 771 | 3-trifluoromethylphenethyl | isopropyl |
| 772 | 3-fluorophenethyl | isopropyl |
| 773 | 3-chlorophenethyl | isopropyl |
| 774 | 3-bromophenethyl | isopropyl |
| 775 | 3-methoxyphenethyl | isopropyl |
| 776 | 3-ethoxyphenethyl | isopropyl |
| 777 | 4-methylphenethyl | isopropyl |
| 778 | 4-trifluoromethylphenethyl | isopropyl |
| 779 | 4-fluorophenethyl | isopropyl |
| 780 | 4-chlorophenethyl | methyl |
| 781 | 4-bromophenethyl | methyl |
| 782 | 4-methoxyphenethyl | methyl |
| 783 | 4-ethoxyphenethyl | methyl |
| 784 | 3,4-dimethoxyphenethyl | methyl |
| 785 | 4-chlorophenethyl | ethyl |
| 786 | 4-bromophenethyl | ethyl |
| 787 | 4-methoxyphenethyl | ethyl |
| 788 | 4-ethoxyphenethyl | ethyl |
| 789 | 3,4-dimethoxyphenethyl | ethyl |
| 790 | 4-chlorophenethyl | isopropyl |
| 791 | 4-bromophenethyl | isopropyl |
| 792 | 4-methoxyphenethyl | isopropyl |

TABLE 1-continued

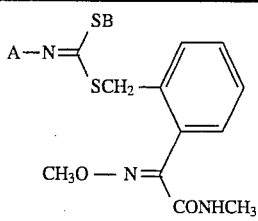

| Compound No. | A | B |
|---|---|---|
| 793 | 4-ethoxphenethyl | isopropyl |
| 794 | 3,4-dimethoxyphenethyl | isopropyl |

TABLE 2

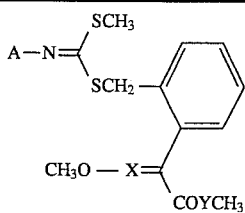

| Compound No. | A | X | Y |
|---|---|---|---|
| 795 | 3-methylbutyl | CH | O |
| 796 | 3-methylbutyl | N | O |
| 797 | 3,3-dimethylbutyl | CH | O |
| 798 | 3,3-dimethylbutyl | N | O |
| 799 | 2-phenylethyl | CH | O |
| 800 | 2-phenylethyl | N | O |
| 801 | 2-methylphenethyl | CH | O |
| 802 | 2-methylphenethyl | N | O |
| 803 | 2-trifluoromethylphenethyl | CH | O |
| 804 | 2-trifluoromethylphenethyl | N | O |
| 805 | 4-trifluoromethylbenzyl | CH | O |
| 806 | 4-trifluoromethylbenzyl | N | O |
| 807 | 2-fluorophenethyl | CH | O |
| 808 | 2-fluorophenethyl | N | O |
| 809 | 2-chlorophenethyl | CH | O |
| 810 | 2-chlorophenethyl | N | O |
| 811 | 2-bromophenethyl | CH | O |
| 812 | 2-bromophenethyl | N | O |
| 813 | 2-methoxyphenethyl | CH | O |
| 814 | 2-methoxyphenethyl | N | O |
| 815 | 2-ethoxyphenethyl | CH | O |
| 816 | 2-ethoxyphenethyl | N | O |
| 817 | 3-methylphenethyl | CH | O |
| 818 | 3-methylphenethyl | N | O |
| 819 | 3-trifluoromethylphenethyl | CH | O |
| 820 | 3-trifluoromethylphenethyl | N | O |
| 821 | 3-fluorophenethyl | CH | O |
| 822 | 3-fluorophenethyl | N | O |
| 823 | 3-chlorophenethyl | CH | O |
| 824 | 3-chlorophenethyl | N | O |
| 825 | 3-bromophenethyl | CH | O |
| 826 | 3-bromophenethyl | N | O |
| 827 | 3-methoxyphenethyl | CH | O |
| 828 | 3-methoxyphenethyl | N | O |
| 829 | 3-ethoxyphenethyl | CH | O |
| 830 | 3-ethoxyphenethyl | N | O |
| 831 | 4-methylphenethyl | CH | O |
| 832 | 4-methylphenethyl | N | O |
| 833 | 4-trifluoromethylphenethyl | CH | O |
| 834 | 4-tdfluoromethylphenethyl | N | O |
| 835 | 4-fluorophenethyl | CH | O |
| 836 | 4-fluorophenethyl | N | O |
| 837 | 4-chlorophehethyl | CH | O |
| 838 | 4-chlorophenethyl | N | O |
| 839 | 4-bromophenethyl | CH | O |
| 840 | 4-bromophenethyl | N | O |
| 841 | 4-methoxyphenethyl | CH | O |
| 842 | 4-methoxyphenethyl | N | O |

TABLE 2-continued

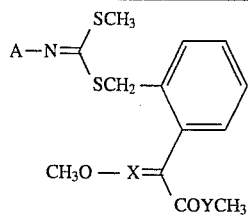

| Compound No. | A | X | Y |
|---|---|---|---|
| 843 | 3,4-dimethoxyphenethyl | CH | O |
| 844 | 3,4-dimethoxyphenethyl | N | O |
| 845 | 4-ethoxyphenyl | CH | O |
| 846 | 4-ethoxyphenyl | N | O |
| 847 | 4-n-propylphenyl | CH | O |
| 848 | 4-n-propylphenyl | N | O |
| 849 | 2-ethoxypyridine-5-yl | CH | O |
| 850 | 2-ethoxypyridine-5-yl | N | O |

$^1$H-NMR data (60 MHz, CDCl$_3$/TMS, δ (ppm)) of some dithiocarbonimide derivatives of the present invention will be presented below.

Compound 1: 2.43 (3H, s), 2.84 (3H, d, J=6 Hz), 2.9–3.1 (1H, br s), 3.92 (3H, s), 4.21 (2H, s), 6.6–7.6 (9H, m).

Compound 2: 2.01 (3H, s), 2.42 (3H, s), 2.76 (3H, d, J=5 Hz), 3.89 (3H, s), 4.18 (2H, s), 6.5–6.8 (2H, m), 6.8–7.6 (7H, m).

Compound 3: 2.31 (3H, s), 2.42 (3H, s), 2.83 (3H, d, J=5 Hz), 3.92 (3H, s), 4.19 (2H, s), 6.4–7.6 (9H, m).

Compound 6: 2.44 (3H, s), 2.87 (3H, d, J=5.5 Hz), 3.76 (3H, s), 3.92 (3H, s), 4.20 (2H, s), 6.3–6.8 (4H, m), 7.0–7.5 (5H, m).

Compound 7: 2.41 (3H, s), 2.80 (3H, d, J=6 Hz), 3.74 (3H, s), 3.91 (3H, s), 4.20 (2H, s), 6.79 (5H, s), 7.0–7.6 (4H, m).

Compound 9: 2.44 (3H, s), 2.87 (3H, d, J=5 Hz), 2.9–3.1 (1H, br s), 3.91 (3H, s), 4.19 (2H, s), 6.4–7.7 (6H, m).

Compound 10: 2.42 (3H, s), 2.82 (3H, d, J=6 Hz), 2.8–3.1 (1H, br s), 3.90 (3H, s), 4.18 (2H, s), 6.70 (2H, d, J=9 Hz), 6.9–7.6 (6H, m).

Compound 18: 1.22 (3H, t, J=7 Hz), 2.40 (3H, s), 2.83 (3H, d, J=5 Hz), 2.8–3.0 (1H, br s), 3.92 (3H, s), 4.21 (2H, d), 6.5–7.4 (8H, m).

Compound 64: 2.45 (3H, s), 2.87 (3H, d, J=5.0 Hz), 3.93 (3H, s), 4.23 (2H, s), 6.82 (1H, d, J=4.6 Hz), 7.10–7.51 (6H, m), 8.17 (1H, d, J=2.0 Hz), 8.32 (1H, d, J=4.4 Hz).

Compound 19: 1.21 (3H, t, J=8 Hz), 2.42 (3H, s), 2.63 (2H, q, J=8 Hz), 2.84 (3H, d, J=6 Hz), 2.9–3.1 (1H, br s), 3.90 (3H, s), 4.18 (2H, s) 6.69 (2H, d, J=8 Hz), 6.9–7.5 (6H, m).

Compound 21: 0.94 (3H, t, J=7 Hz), 1.3–1.9 (2H, m), 2.41 (3H, s), 2.59 (2H, t, J=6 Hz), 2.83 (3H, d, J=5 Hz), 2.8–3.1 (1H, br s), 3.92 (3H, s,) 3.92 (3H, s), 4.20 (2H, s), 6.71 (2H, d, J=8 Hz), 6.9–7.6 (6H, m).

Compound 25: 0.5–1.8 (7H, m), 2.85 (3H, d, J=5 Hz), 2.8–3.2 (3H, m), 3.77 (3H, s), 3.92 (3H, s), 4.19 (2H, s), 6.80 (4H, s), 7.0–7.6 (4H, m).

Compound 26: 1.39 (3H, t, J=7 Hz), 2.41 (3H, s), 2.81 (3H, d, J=6 Hz), 2.9–3.1 (1H, br s), 3.91 (3H, s), 3.48 (2H, q, J=7 Hz), 4.18 (2H, s), 6.79 (4H, s), 7.0–7.7 (4H, m).

Compound 30: 0.97 (3H, t, J=6 Hz), 1.3–2.0 (4H, m), 2.42 (3H, s), 2.82 (3H, d, J=5 Hz), 2.8–3.1 (1H, br s), 3.90 (3H, s), 3.90 (2H, t, J=6 Hz), 4.18 (2H, s), 6.78 (4H, s), 7.0–7.5 (4H, m).

Compound 31: 2.41 (3H, s), 2.82 (3H, d, J=6 Hz), 3.8–3.9 (1H, br s), 3.88 (3H, s), 4.15 (2H, s), 6.7–7.5 (13H, m).

Compound 33: 2.43 (6H, s), 2.82 (3H, d, J=5 Hz), 3.90 (3H, s), 4.20 (2H, s), 6.78 (2H, d, J=8 Hz), 7.0–7.5 (4H, m).

Compound 42: 2.41 (3H, s), 2.80 (3H, d, J=5 Hz), 3.89 (3H, s), 4.20 (2H, s), 6.81 (2H, d, J=8 Hz), 7.0–7.4 (5H, m), 7.49 (2H, d, J=8 Hz).

Compound 48: 2.47 (3H, s), 2.87 (3H, d, J=4.8 Hz), 3.93 (3H, s), 4.22 (2H, s), 6.74 (1H, m), 6.91 (2H, d, J=8.4 Hz), 7.16 (1H, d, J=6.9 Hz), 7.28–7.41 (2H, m), 7.47 (1H, d, J=6.7 Hz), 7.55 (2H, d, J=8.4 Hz).

Compound 50: 2.41 (3H, s), 2.80 (3H, d, J=6 Hz), 2.7–3.0 (1H, br s), 3.89 (3H, s), 4.19 (2H, s), 6.78 (2H, d, J=8 Hz), 7.0–7.5 (6H, m).

Compound 52: 2.23 (6H, s), 2.40 (3H, s), 2.80 (3H, d, J=5 Hz), 3.89 (3H, s), 4.18 (2H, s), 6.42 (2H, s), 6.68 (1H, s), 7.0–7.6 (5H, m).

Compound 55: 2.45 (3H, s), 2.85 (3H, d, J=5 Hz), 2.7–2.9 (1H, br s), 3.84 (6H, s), 3.92 (3H, s), 4.19 (2H, s), 6.39 (1H, d, J=9 Hz), 6.45 (1H, s), 6.80 (1H, d, J=9 Hz), 7.0–7.5 (4H, m).

Compound 62: 2.30 (3H, s), 2.42 (3H, s), 2.82 (3H, d, J=6 Hz), 3.88 (3H, s), 4.14 (2H, s), 6.5–7.6 (8H, m).

Compound 72: 2.29 (3H, s), 2.46 (3H, s), 2.86 (3H, d, J=5.0 Hz), 3.90 (3H, s), 4.28 (2H, s), 6.83 (1H, d, J=8.1 Hz), 7.14 (1H, br s), 7.13–7.53 (5H, m), 8.23 (1H, s).

Compound 74: 2.47 (3H, s), 2.88 (3H, s), 3.92 (3H, s), 3.95 (3H, s), 4.24 (2H, s), 6.65–6.79 (2H, m), 7.10–7.22 (2H, m), 7.26–7.43 (2H, m), 7.49 (1H, s), 7.74 (1H, d, J=2.5 Hz).

Compound 76: 2.48 (3H, s), 2.88 (3H, d, J=5.0 Hz), 3.92 (3H, s), 4.27 (2H, s), 6.89 (1H, d, J=8.5 Hz), 6.97 (1H, br s), 7.13–7.50 (3H, m), 7.61 (1H, dd, J=5.9, 2.6 Hz), 8.36 (1H, s).

Compound 77: 1.39 (3H, t, J=8.4 Hz), 2.46 (3H, s), 2.89 (3H, s), 3.96 (3H, s), 4.17 (2H, br s), 4.32 (2H, q, J=8.4 Hz), 6.64–6.80 (2H, m), 7.11–7.20 (2H, m), 7.27–7.50 (3H, m), 7.72 (1H, s).

Compound 80: 2.50 (3H, s), 2.89 (3H, d, J=5.0 Hz), 3.94 (3H, s), 4.24 (2H, s), 6.87 (1H, br s), 7.10–7.54 (6H, m), 7.96 (1H, d, J=2.4 Hz).

Compound 78: 1.33 (6H, d, J=6.1 Hz), 2.46 (3H, s), 2.87 (3H, br s), 3.94 (3H, s), 4.25 (2H, s), 5.24 (1H, sep, J=6.1 Hz), 6.63 (1H, d, J=8.6 Hz), 6.78 (1H, d, J=4.7 Hz), 7.10–7.20 (2H, m), 7.26–7.52 (3H, m), 7.72 (1H, d, J=2.6 Hz).

Compound 79: 2.47 (3H, s), 2.86 (3H, s), 3.93 (3H, s), 4.23 (2H, s), 4.72 (2H, q, J=8.6 Hz), 6.70–6.87 (2H, m), 7.10–7.41 (4H, m), 7.46 (1H, s), 7.68 (1H, d, J=2.6 Hz).

Compound 81: 2.21 (1.2H, s), 2.26 (1.8H, s), 2.54 (1.2H, s), 2.60 (1.8H, s), 2.90 (3H, d, J=5.0 Hz), 3.70 (1.8H, s), 3.75 (1.2H, s), 3.97 (3H, s), 4.31 (2H, s), 5.93 (0.4H, s), 5.98 (0.6H, s), 6.80 (1H, s), 7.10–7.21 (1H, m), 7.27–7.54 (3H, m).

Compound 82: 2.18 (3H, s), 2.24 (3H, s), 2.90 (3H, d, J=5.0 Hz), 2.95 (3H, s), 3.99 (3H, s), 4.28 (2H, s), 6.74 (1H, br s), 7.14 (1H, d, J=7.2 Hz), 7.20–7.40 (2H, m), 7.50 (1H, d, J=6.8 Hz).

Compound 415: 0.87–0.94 (3H, m), 1.31–1.67 (4H, m), 1.55–1.72 (2H, m), 2.36 (1.2H, s), 2.47 (1.8H, s), 2.92 (1.8H, d, J=5.0 Hz), 2.93 (1.2H, d, J=5.0 Hz), 3.36–3.39 (2H, m), 3.97 (1.8H, s), 3.98 (1.2H, s), 4.13 (1.2H, s), 4.18 (0.8H, s), 6.75 (1H, br s), 7.12–7.49 (4H, m).

Compound 416: 0.86–0.93 (3H, m), 1.24–1.72 (8H, m), 2.36 (1.2H, s), 2.47 (1.8H, s), 2.93 (3H, t, J=5.1 Hz), 3.39 (2H, t, J=6.6 Hz), 3.97 (1.8H, s), 3.98 (1.2H, s), 4.12 (0.8H, s), 4.20 (1.2H, s), 6.76 (1H, br s), 7.11–7.50 (4H, m).

Compound 417: 0.85–0.92 (3H, m), 1.22–1.41 (6H, m), 1.53–1.72 (2H, m), 2.36 (1.2H, s), 2.47 (1.8H, s), 2.93 (3H, d, J=5.0 Hz), 3.38 (0.8H, t, J=6.8 Hz), 3.39 (1.2H, t, J=6.8 Hz), 3.97 (1.8H, s), 3.98 (1.2H, s), 4.11 (0.8H, s), 4.18 (1.2H, s), 6.76 (1H, br s), 7.13–7.50 (4H, m).

Compound 418: 0.89 (3H, m), 1.20–1.72 (12H, m), 2.36 (1.2H, s), 2.47 (1.8H, s), 2.93 (3H, d, J=5.0 Hz), 3.33–3.41 (2H, m), 3.97 (1.8H, s), 3.98 (1.2H, s), 4.11 (1.2H, s), 4.18 (0.8H, s), 7.1–7.5 (4H, m).

Compound 420: 0.88 (3H, t, J=6.0 Hz), 1.22–1.71 (16H, m), 2.36 (1.2H, s), 2.47 (1.8H, s), 2.93 (3H, d, J=5.0 Hz), 3.32–3.41 (2H, m), 3.96 (1.2H, s), 3.98 (1.8H, s), 4.12 (1.2H, s), 4.18 (0.8H, s), 7.1–7.5 (4H, m).

Compound 423: 0.92 (2.4H, d, J=6.7 Hz), 0.97 (3.6H, d, J=6.7 Hz), 1.85–2.05 (1H, m), 2.37 (1.2H, s), 2.48 (1.8H, s), 2.93 (1.8H, d, J=5.0 Hz), 2.94 (1.2H, d, J=5.0 Hz), 3.17 (0.8H, d, J=6.6 Hz), 3.18 (1.2H, d, J=6.6 Hz), 3.97 (1.8H, s), 3.98 (1.2H, s), 4.14 (0.8H, s), 4.18 (1.2H, s), 6.76 (1H, br s), 7.11–7.50 (4H, m).

Compound 425: 0.80–0.92 (3H, m), 1.02 (1.2H, d, J=6.0 Hz), 1.10 (1.8H, d, J=6.0 Hz), 1.15–1.62 (4H, m), 2.34 (1.2H, s), 2.47 (1.8H, s), 2.92 (3H, d, J=5.0 Hz), 3.68–3.82 (1H, m), 3.97 (3H, s), 4.11 (0.6H, s), 4.17 (0.4H, s), 6.75 (1H, br s), 7.10–7.51 (4H, m).

Compound 428: 0.89 (2.4H, d, J=6.6 Hz), 0.93 (3.6H, d, J=6.6 Hz), 1.44–1.81 (3H, m), 2.36 (1.2H, s), 2.48 (1.8H, s), 2.93 (3H, d, J=5.0 Hz), 3.39 (0.8H, t, J=6.6 Hz), 3.42 (1.2H, t, J=6.6 Hz), 3.97 (1.8H, s), 3.98 (1.2H, s), 4.11 (1.2H, s), 4.18 (0.8H, s), 6.75 (1H, br s), 7.11–7.50 (4H, m).

Compound 431: 0.91 (3.6, s), 0.95 (5.4H, s), 1.48–1.64 (2H, m), 2.35 (1.2H, s), 2.48 (1.8H, s), 2.93 (3H, d, J=5.0 Hz), 3.39–3.49 (2H, m), 3.97 (1.8H, s), 3.98 (1.2H, s), 4.10 (1.2H, s), 4.19 (0.8H, s), 6.76 (1H, br s), 7.10–7.52 (4H, m).

Compound 459: 2.24 (0.4H, t, J=2.6 Hz), 2.29 (0.6H, t, J=2.6 Hz), 2.41 (1.2H, s), 2.50 (1.8H, s), 2.93 (1.8H, d, J=5.0 Hz), 2.94 (1.2H, d, J=5.0 Hz), 3.98 (3H, s), 4.16–4.24 (4H, m), 6.82 (1H, br s), 7.09–7.55 (4H, m).

Compound 462: 2.37 (1.2H, s), 2.47 (1.8H, s), 2.91 (1.8H, d, J=5.0 Hz), 2.93 (1.2H, d, J=5.0 Hz), 3.38 (1.2H, s), 3.42 (1.8H, s), 3.57–3.72 (4H, m), 3.97 (1.8H, s), 3.98 (1.2H, s), 4.14 (1.2H, s), 4.19 (0.8H, s), 6.82 (0.4H, br s), 6.93 (0.6H, br s), 7.08–7.47 (4H, m).

Compound 471: 1.00–1.36 (6H, m), 2.36 (1.2H, s), 2.48 (1.8H, s), 2.53–2.68 (4H, m), 2.70–3.90 (2H, m), 2.92 (1.8H, d, J=5.0 Hz), 2.93 (1.2H, d, J=5.0 Hz), 3.55–3.66 (2H, m), 3.97 (1.8H, s), 3.98 (1.2H, s), 4.12 (1.2H, s), 4.19 (0.8H, s), 6.79 (1H, br s), 7.10–7.53 (4H, m).

Compound 472: 1.61–2.08 (4H, m), 2.37 (1.2H, s), 2.48 (1.8H, s), 2.91 (1.8H, t, J=5.0 Hz), 2.93 (1.2H, t, J=5.0 Hz), 3.38–3.58 (2H, m), 3.73–3.94 (2H, m), 3.96 (1.8H, s), 3.98 (1.2H, s), 4.06–4.37 (3H, m), 6.84 (0.4H, br s), 6.95 (0.6H, br s), 7.13–7.52 (4H, m).

Compound 475: 2.36 (1.2H, s), 2.45 (1.8H, s), 2.88–3.02 (5H, m), 3.64 (0.8H, t, J=7.6 Hz), 3.66 (1.2H, t, J=7.6 Hz), 3.95 (1.2H, s), 3.96 (1.8H, s), 4.11 (1.2H, s), 4.16 (0.8H, s), 6.76 (1H, br s), 7.08–7.48 (9H, m).

Compound 485: 2.40 (1.2H, s), 2.52 (1.8H, s), 2.90 (1.8H, d, J=5.0 Hz), 2.92 (1.2H, d, J=5.0 Hz), 3.91 (1.8H, s), 3.98 (1.2H, s), 4.16 (1.2H, s), 4.23 (0.8H, s), 4.56 (0.8H, s), 4.59 (1.2H, s), 6.19 (0.4H, d, J=3.1 Hz), 6.23 (0.6H, d, J=3.1 Hz), 6.32 (0.4H, dd, J=3.1, 1.9 Hz), 6.35 (0.6H, dd, J=3.1, 1.9 Hz), 6.74 (0.6H, br s), 6.82 (0.4H, br s), 7.11–7.51 (5H, m).

Compound 795: 0.89 (2.4H, d, J=6.6 Hz), 0.94 (3.6H, d, J=6.6 Hz), 1.46–1.81 (3H, m), 2.36 (1.2H, s), 2.48 (1.8H, s), 3.40 (0.8H, t, J=6.6 Hz), 3.44 (1.2H, t, J=6.6 Hz), 3.70 (3H, s), 3.83 (1.8H, s), 3.84 (1.2H, s), 4.16 (1.2 H, s), 4.22 (0.8H, s), 7.08–7.50 (4H, m), 7.58 (0.6H, s), 7.51 (0.4H, s).

Compound 796: 0.89 (2.4H, d, J=6.6 Hz), 0.93 (3.6H, d, J=6.6 Hz), 1.30–1.81 (3H, m), 2.35 (1.2H, s), 2.47 (1.8H, s), 3.38–3.46 (3H, m), 3.87 (3H, s), 4.05 (3H, s), 4.11 (1.2H, s), 4.17 (0.8H, s), 7.08–7.52 (4H, m).

Compound 797: 0.91 (3.6H, s), 0.96 (5.4H, s), 1.26 (2H, d, J=7.2 Hz), 2.36 (1.2H, s), 2.48 (1.8H, s), 3.43 (1.2H, d, J=7.2 Hz), 3.47 (0.8H, d, J=7.2 Hz), 3.70 (3H, s), 3.83 (1.8H, s), 3.84 (1.2H, s), 4.15 (1.2H, s), 4.23 (0.8H, s), 7.08–7.47 (4H, m), 7.57 (0.6H, s), 7.61 (0.4H, s).

Compound 798: 0.91 (3.6H, s), 0.96 (5.4H, s), 1.48–1.62 (2H, m), 2.35 (1.2H, s), 2.47 (1.8H, s), 3.38–3.49 (2H, m), 3.87 (3H, s), 4.05 (1.8H, s), 4.07 (1.2H, s), 4.10 (1.2H, s), 4.17 (0.8H, s), 7.09–7.55 (4H, m).

Compound 799: 2.37 (1.2H, s), 2.45 (1.8H, s), 2.91 (0.8H, t, J=7.4 Hz), 3.01 (1.2H, t, J=7.4 Hz), 3.58–3.70 (2H, m), 3.67 (1.2H, s), 3.70 (1.8H, s), 4.16 (1.2H, s), 4.19 (0.8H, s), 7.09–7.46 (9H, m), 7.57 (0.6H, s), 7.59 (0.4H, s).

Compound 800: 2.36 (1.2H, s), 2.44 (1.8H, s), 2.90 (0.8H, t, J=7.6 Hz), 2.99 (1.2H, t, J=7.6 Hz), 3.65 (3H, t, J=7.6 Hz), 3.82 (1.2H, s), 3.87 (1.8H, s), 4.04 (1.2H, s), 4.06 (1.8H, s), 4.11 (1.2H, s), 4.14 (0.8H, s), 7.10–7.50 (9H, m).

Compound 809: 2.35 (1.2H, s), 2.45 (1.8H, s), 3.06 (0.8H, t, J=7.2 Hz), 3.17 (1.2H, t, J=7.2 Hz), 3.64 (1.2H, t, J=7.2 Hz), 3.65 (0.8H, t, J=7.2 Hz), 3.67 (1.2H, s), 3.70 (1.8H, s), 3.80 (1.2H, s), 3.81 (1.8H, s), 4.15 (1.2H, s), 4.18 (0.8H, s), 7.09–7.47 (8H, m), 7.57 (0.6H, s), 7.59 (0.4H, s).

Compound 823: 2.36 (1.2H, s), 2.46 (1.8H, s), 2.87 (0.8H, t, J=2.1 Hz), 2.98 (1.2H, t, J=7.1 Hz), 3.60 (0.8H, t, J=7.1 Hz), 3.64 (1.2H, t, J=7.1 Hz), 3.67 (1.2H, s), 3.70 (1.8H, s), 3.80 (1.2H, s), 3.82 (1.8H, s), 4.14 (0.8H, s), 4.19 (1.2H, s), 7.08–7.46 (8H, m), 7.57 (0.6H, s), 7.59 (0.4H, s).

Compound 837: 2.35 (1.2H, s), 2.45 (1.8H, s), 2.87 (0.8H, t, J=7.2 Hz), 2.96 (12.2H, t, J=7.0 Hz), 3.59 (0.8H, t, J=7.2 Hz), 3.62 (1.2H, t, J=7.0 Hz), 3.67 (1.2H, s), 3.70 (0.8H, s), 3.80 (1.2H, s), 3.82 (1.8H, s), 4.13 (1.2H, s), 4.19 (0.8H, s), 7.09–7.47 (8H, m), 7.57 (0.6H, s), 7.59 (0.4H, s).

The following will describe typical production examples of the thiocarbamate derivative of the formula II.

Production of N-phenyl-S-(2-(α-methoxyimino-α-methoxycarbonylmethyl)phenylmethyl)dithiocarbamate To a diethyl ether solution (50 ml) containing aniline (5.0 g, 54 mmol) and triethylamine (11.0 g, 108 mmol), carbondisulfide (4.2 g, 55 mmol) was added and the mixture was stirred at room temperature overnight. The precipitated solid content was filtered, washed with diethyl ether and dried to give 11 g of the triethylammonium salt of N-phenyldithiocarbonimide.

The above triethylammonium salt of N-phenyldithiocarbonimide (3.7 g, 10 mmol) was dissolved in DMF (30 ml), and (E)-2-(2-bromomethylphenyl)-2-methyl methoxyiminoacetate (2.9 g, 10 mmol) was added to the resulting solution and the mixture was stirred at room temperature for 2 hours. This reaction mixture was diluted with diethyl ether and water was added to separate the reaction mixture. The organic layer was dried over anhydrous magnesium sulfate and the solvent was distilled off under reduced pressure to give an oily product. This oily product was subjected to silica gel chromatography (3:1 hexane/ethyl acetate) to give 2.9 g of N-phenyl-S-(2-(α-methoxy-imino-α-methoxycarbonylmethyl)phenylmethyl)dithiocarbamate.

$^1$H-NMR (60 MHz, CDCl$_3$/TMS, δ (ppm)): 3.81 (3H, s), 4.00 (3H, s), 4.43 (2H, s), 7.0–7.6 (9H, m), 8.95 (1H, br s).

Production of N-(4-methoxyphenyl)-S-methyldithiocarbamate

To a diethyl ether solution (30 ml) containing p-anisidine (2.0 g, 16 mmol) and triethylamine (3.3 g, 32 mmol), carbonbisulfide (1.3 g, 16 mmol) was added and the mixture was stirred at room temperature overnight. The precipitated solid content was filtered, washed with diethyl ether and dried to give 5.6 g of the triethylammonium salt of N-(4-methoxyphenyl)dithiocarbonimide.

The above triethylammonium salt of N-(4-methoxyphenyl)dithiocarbonimide (2.0 g, 5 mmol) was dissolved in methanol (10 ml), and a methanol solution (5 ml) of methyl iodide (0.8 g, 5 mmol) was added dropwise to the resulting solution and the mixture was stirred at room temperature for 2 hours. After the solvent was distilled off under reduced pressure, the residue was diluted with dichloroethane and water was added to separate the residue. The organic layer was dried over anhydrous magnesium sulfate and the solvent was distilled off under reduced pressure to give a solid product. Hexane was added to this solid product to give a dispersion, which was filtered and dried to give 0.9 g of N-(4-methoxyphenyl)-S-methyldithiocarbamate.

$^1$H-NMR (60 MHz, CDCl$_3$/TMS, δ (ppm)): 2.51 (3H, s), 2.81 (3H, s), 6.86 (2H, d, J=9 Hz), 7.28 (2H, d, J=9 Hz), 8.90 (1H, br s).

Typical examples of the dithiocarbamate derivative of the formula II are shown in Tables 3 and 4.

TABLE 3

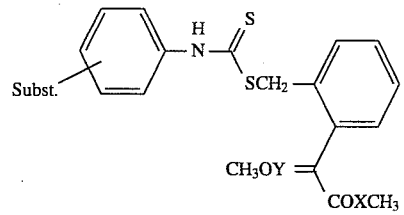

| Substituent | Substituent |
|---|---|
| hydrogen (non-substituted) | 3-bromo |
| 2-methyl | 4-bromo |
| 3-methyl | 2-ethyl |
| 4-methyl | 3-ethyl |
| 2-methoxy | 4-ethyl |
| 3-methoxy | 2-n-propyl |
| 4-methoxy | 4-n-propyl |
| 2-chloro | 4-isopropyl |
| 3-chloro | 4-n-butyl |
| 4-chloro | 2-ethoxy |
| 2-fluoro | 3-ethoxy |
| 3-fluoro | 4-ethoxy |
| 4-fluoro | 3-n-propyloxy |
| 4-tert-butyl | 4-n-propyloxy |
| 4-isopropyloxy | 2-trifluoromethyl |
| 4-n-butyloxy | 3-trifluoromethyl |
| 4-phenoxy | 4-trifluoromethyl |
| 3-methylthio | 3-trifluoromethoxy |
| 4-methylthio | 4-trifluoromethoxy |
| 2-ethylthio | 2,5-dimethyl |
| 3-ethylthio | 3,5-dimethyl |
| 4-ethylthio | 3,4-dimethyl |
| 4-n-propylthio | 3,5-dimethoxy |
| 3-n-butylthio | 3,4-dimethoxy |
| 4-methoxycarbonyl | 2,4-dichloro |
| 2-cyano | 3,4-dichloro |
| 3-cyano | 3,5-dichloro |
| 4-cyano | 3,4-methylenedioxy |
| 4-nitro | 3,4,5-trichloro |
| 3-nitro | 3,4,5-trimethoxy |
| 3,4-difluoromethylenedioxy | 3-chloro-4-methyl |

TABLE 4

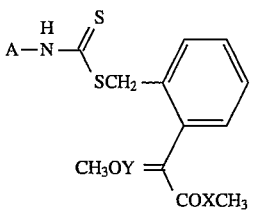

(X = NH or O, Y = CH or N, but when X = NH, Y is not CH.)

A 2-pyridyl
3-pyridyl
4-pyridyl
pyridazin-3-yl
4,6-dimethylpyrimidin-2-yl
thiazol-2-yl
3-methylisothiazol-5-yl
1,3,4-thiadiazol-2-yl
4-methylpyridin-2-yl
5-methylpyridin-2-yl
2-methylpyridin-3-yl The following will describe formulation examples of the dithiocarbonimide derivative of the present invention where parts are all by weight.

Formulation Example 1

First, 50 parts of each of the compounds (1) to (8) are mixed with 3 parts of calcium lignin sulfonate, 2 parts of sodium laurylsulfate and 45 parts of synthetic hydrated silicon oxide. The mixture is thoroughly pulverized and mixed to give wettable powders for each compound.

Formulation Example 2

First, 25 parts of each of the compounds (1)to (850) are mixed with 3 parts of polyoxyethylene sorbitan monooleate, 3 parts of CMC and 69 parts of water. The mixture is subjected to wet pulverization Until a particle size of the active ingredient becomes not more than 5 lam to give suspensions for each compound.

Formulation Example 3

First, 2 parts of each of the compounds (1) to (850) are mixed with 88 parts of kaolin clay and 10 parts of talc. The mixture is thoroughly pulverized and mixed to give dusts for each compound.

Formulation Example 4

First, 20 parts of each of the compounds (1 ) to (850) are mixed with 14 parts of polyoxyethylene styrylphenyl ether, 6 parts of calcium dodecylbenzenesulfonate and 60 parts of xylene. The mixture is thoroughly mixed to give emulsifiable concentrates for each compound.

Formulation Example 5

First, 2 parts of each of the compounds (1) to (850) are mixed with 1 part of synthetic hydrated silicon oxide, 2 parts of calcium lignin sulfonate, 30 parts of bentonite and 65 parts of kaolin clay. The mixture is thoroughly pulverized and mixed. Then, water is added to the mixture, which is thoroughly kneaded, granulated and dried to give granules for each compound.

Formulation Example 6

First, 20 parts of each of the compounds (1) to (850) are mixed with 1.5 parts of sorbitan trioleate and 28.5 parts of an aqueous solution containing 2 parts of polyvinyl alcohol, and the mixture is pulverized into fine powders having a particle size of not more than 3 gm with a sand grinder. Each of the mixture is mixed with 40 parts of an aqueous solution containing 0.05 parts of xanthan gum and 0.1 parts of aluminum magnesium silicate, and then mixed with 10 parts of propylene glycol to give 20% water-based suspensions for each compound.

Formulation Example 7

First, 0.1 parts of each of the compounds (1) to (850) is dissolved in 5 parts of xylene and 5 parts of trichloroethane, and the solution is mixed with 89.8 parts of deodorized kerosine to give 0.1% oil solutions for each compound.

Formulation Example 8

First, 0.1 parts of each of the compounds (1) to (850) is dissolved in 59.6 parts of deodorized kerosine together with 0.2 parts of tetramethrin, 0.1 parts of d-phenothrin and 10 parts of trichloroethane, and an aerosol vessel is filled with the solution. Then, the vessel is equipped with a valve, through which 30 parts of a propellent (liquefied petroleum gas) are charged under pressure to give an oil-based aerosol for each compound.

Formulation Example 9

An aerosol vessel is filled with 50 parts of pure water and a mixture of 0.2 parts of a compound from the compounds (1) to (850), 0.2 parts of d-allethrin, 0.2 parts of d-phenothrin, 5 parts of xylene, 3.4 parts of deodorized kerosine and 1 part of an emulsifier (ATMOS 300, registered trade mark by Atlas Chemical Co.). Then, the vessel is equipped with a valve, through which 40 parts of a propellent (liquefied petroleum gas) are charged under pressure to give a water-based aerosol for each compound.

Formulation Example 10

First, 0.4 g of each of the compounds (1) to (850) is dissolved in 20 ml of acetone together with 0.3 g of d-allethrin, and the solution is uniformly mixed with 99.4 g of a carrier for mosquito-coil (prepared by mixing a flour of Machilus thunberii Sieb. et Zucc., a dregs flour and a wood flour in a proportion of 4: 3: 3) while stirring. Then, 120 ml of water is added to the mixture, which is kneaded sufficiently, molded and dried to give a mosquito-coil of each compound.

Formulation Example 11

First, 0.4 g of each of the compounds (1) to (850) is dissolved in acetone together with 0.4 g of d-allethrin and 0.4 g of pipenyl butoxide to give 10 ml of a solution. A substrate for electric heating mat having a size of 2.5 cm×1.5 cm×0.3 cm in thickness (prepared by forming a fibrillated mixture of cotton linter and pulp into a sheet) is uniformly impregnated with 0.5 ml of the solution to give an electric mosquito-repellent mat of each compound.

Formulation Example 12

First, 100 mg of each of the compound (1) to (850) is dissolved in a suitable amount of acetone, and a porous ceramic plate having a size of 4.0 cm×4.0 cm×1.2 cm in thickness is impregnated with the resulting solution to give a heating smoke formulation of each compound.

Formulation Example 13

First, 10rag of each of the compound (1) to (850) is dissolved in 0.5 ml of acetone, and the solution is uniformly mixed with 5 g of solid bait powder (Breeding Solid Feed Powder CE-2, trade name by Japan Clea Co., Ltd.). Then, acetone is removed to give a 0.5% poison bait of each of compound.

The following biological test examples illustrate that the dithiocarbonimide derivative of the present invention is useful as an agricultural/horticultural fungicide. The compounds used for comparison are indicated by the symbols in Table 5.

TABLE 5

| Symbol of compound | Chemical structural formula | Remarks |
| --- | --- | --- |
| A | Ph—NH—C(=O)—OCH$_2$—Ph, C(=NOCH$_3$)—C(=O)—O—CH$_3$ | Compound 5 described in Table 33 of WO 93/071116 |
| B | Ph—NH—C(=O)—OCH$_2$—Ph, C(=NOCH$_3$)—C(=O)—NH—CH$_3$ | Compound 5 described in Table 65 of the above specification |

The degree of plant diseases at the time of examination, i.e. degree of colony formation and lesion of stalks and leaves was determined by visual observation, and the preventive or curative activities were evaluated according to the following criteria:

5: No colony formation and no lesion were observed.
4: Colony formation and lesion were observed in a severity of about 10%.
3: Colony formation and lesion were observed in a severity of about 30%.
2: Colony formation and lesion were observed in a severity of about 50%.
1: Colony formation and lesion were observed in a severity of about 70%.
0: Colony formation and lesion were observed in a severity of more than and the severity was similar to that found when no test compound was used.

Biological Test Example 1

Preventive test against rice blast

A plastic pot was filled with sandy loam, and rice (Nihonbare) was seeded and raised in a greenhouse for 20 days. Thereafter, wettable powders prepared from a test compound in the same manner as described in Formulation Example 1 were diluted with water to the predetermined concentration of 500 ppm, and the resulting solution was sprayed over the stem and leaves so as to sufficiently adhere to the leaf surface of the rice seedlings. After the solution was sprayed, the rice seedlings were air-dried and a spore suspension of rice blast pathogen was sprayed to inoculate them with the pathogen. After the inoculation, the rice seedlings were maintained at 28° C. under high humidity for 6 days and the preventive activity was examined.

As a result, the following compounds exhibited the preventive value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83, 329, 411, 412, 414, 416, 417, 418, 419, 420, 421, 423, 425, 428, 431, 457, 459, 462, 463, 464, 471, 472, 474, 475, 485, 645, 795, 797, 798, 799, 800, 809, 823 and 837.

The compounds A and B exhibited the preventive value "0".

Biological Test Example 2

Curative test against rice blast

A plastic pot was filled with sandy loam, and rice (Nihonbare) was seeded and raised in a greenhouse for 20 days. Then, a spore suspension of rice blast pathogen was sprayed onto the rice seedlings to inoculate them with the pathogen. After the inoculation, the rice seedlings were maintained at 28° C. under high humidity for one day. Thereafter, wettable powders prepared from a test compound in the same manner as described in Formulation Example 1 were diluted with water to the predetermined concentration of 500 ppm and the resulting solution was sprayed over the stem and leaves so as to sufficiently adhere to the leaf surface of the rice seedlings. After the solution was sprayed, the rice seedlings were maintained at 28° C. under high humidity for 5 days and As a result, the following compounds exhibited the curative value "5". the curative activity was examined.

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83 and 329.

The compounds A and B exhibited the curative activity value "0".

Biological Test Example 3

Preventive test against rice sheath blight

A plastic pot was filled with sandy loam, and rice (Nihonbare) was seeded and raised in a greenhouse for 20 days. Wettable powders prepared from a test compound in the same manner as described in Formulation Example 1 were diluted with water to the predetermined concentration of 500 ppm and the resulting solution was sprayed over the stem and leaves so as to sufficiently adhere to the leaf surface of the rice seedlings. After the solution was sprayed, the rice plant was air-dried and inoculated with bran-cultured hyphae of sheath blight pathogen at the plant foot. After the inoculation, the rice seedlings were maintained at 28° C. under high humidity for 4 days and the preventive activity was examined.

As a result, the following compounds exhibited the preventive activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83, 329, 411, 412, 414, 416, 417, 418, 419, 420, 421, 423, 425, 428, 431, 457, 459, 463, 464, 471, 472, 474, 475, 485, 645, 795, 797, 798, 799, 800, 809, 823 and 837.

The compounds A and B exhibited the preventive activity value "0".

Biological Test Example 4

Preventive test against late blight on tomato

A plastic pot was filled with sandy loam, and tomato (Ponteroza) was seeded and raised in a greenhouse for 20 days. Wettable powders prepared from a test compound in the same manner as described in Formulation Example 1 were diluted with water to the predetermined concentration of 500 ppm and the resulting solution was sprayed over the stem and leaves so as to sufficiently adhere to the leaf surface of the tomato seedlings where the second or third true leaf was put out. After the solution was sprayed, a spore suspension of *Phytophthora infestaris* was inoculated by spraying. After the inoculation, the tomato seedlings were maintained at 20° C. under high humidity for one day and raised under lighting for additional 5 days, and the control effect was examined.

As a result, the following compounds exhibited the preventive activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83, 329, 411, 414, 416, 417, 418, 420, 421, 423, 425, 428, 431, 457, 459, 472, 474, 475, 645, 795, 797, 798, 799, 800, 809, 823 and 837.

The compounds A and B exhibited the preventive activity value "0".

Biological Test Example 5

Curative test against powdery mildew on wheat

A plastic pot was filled with sandy loam, and wheat (Norin No. 73) was seeded and raised in a greenhouse for 10 days. The wheat seedling where the second leaf was put out was inoculated with *Erysiphe graminis*. After the inoculation, the wheat seedlings were raised in a greenhouse at 23° C. for 3 days. Then, suspensions prepared from a test compound in the same manner as described in Formulation Example 2 were diluted with water to the predetermined concentration of 500 ppm and the resulting solution was sprayed over the stem and leaves so as to sufficiently adhere to the leaf surface of the wheat seedlings. After the solution was sprayed, the wheat seedlings were raised under lighting for additional 7 days and the curative activity was examined.

As a result, the following compounds exhibited curative activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83, 329, 411, 412, 414, 416, 417, 418, 419, 420, 421, 423, 425, 428, 431, 457, 459, 462, 463, 464, 471, 472, 474, 475, 485, 645, 795, 797, 798, 799, 800, 809, 823 and 837.

The compounds A and B exhibited curative activity value "0".

Biological Test Example 6

Preventive test against rust on wheat

A plastic pot was filled with sandy loam, and wheat (Norin No. 73) was seeded and raised in a greenhouse for 10 days. Emulsifiable concentrates prepared from a test compound in the same manner as described in Formulation Example 4 were diluted with water to the predetermined concentration of 500 ppm and the resulting solution was sprayed over the stem and leaves so as to sufficiently adhere to the leaf surface of the wheat seedlings where the second or third true leaf was put out. After air-drying, the wheat seedlings were inoculated with spore of *Puccinia striiformis*. After the inoculation, the wheat seedlings were maintained at 23° C. under dark and high humidity for one day and raised under lighting for additional 6 days and the control effect was examined. As a result, the following compounds exhibited the preventive activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83, 329, 411, 412, 414, 416, 417, 419, 420, 421, 423, 425, 428, 431, 457, 459, 462, 463, 464, 471, 472, 474, 475, 645, 795, 797, 798, 799, 800, 809, 823 and 837.

The compounds A and B exhibited the preventive activity value "0".

Biological Test Example 7

Preventive test against Speckled leaf blotch

A plastic pot was filled with sandy loam, and wheat (Norin No. 73) was seeded and raised in a greenhouse for 10 days. Emulsifiable concentrates prepared from a test compound in the same manner as described in Formulation Example 4 were diluted with water to the predetermined concentration of 500 ppm and the resulting solution was sprayed over the stem and leaves so as to sufficiently adhere to the leaf surface of the wheat seedlings. Then the wheat seedlings were inoculated with a spore suspension of the pathogen. After the inoculation, the wheat seedlings were maintained at 15° C. under dark and high humidity for 3 days and raised under lighting for additional 18 days and the control effect was examined. As a result, the following compounds exhibited the preventive activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83 and 329.

The compounds A and B exhibited the preventive activity value "0".

Biological Test Example 8

Curative test against downy mildew on grape

A plastic pot was filled with sandy loam, and grape (Berry A) was seeded and raised in a greenhouse for 40 days. A zoosporangium suspension of *Plasmopara viticola* was inoculated by spraying to the grape seedling where about three true leaves were put out. After the inoculation, the grape seedlings were maintained at 23° C. under high humidity overnight. Then, emulsifiable concentrates prepared from a test compound in the same manner as described in Formulation Example 4 were diluted with water to the predetermined concentration of 500 ppm and the resulting solution was sprayed over the stem and leaves so as to sufficiently adhere to the leaf surface of the grape seedlings. After the solution was sprayed, the grape seedlings were raised for additional 7 days and the control effect was examined. As a result, the following compounds exhibited the curative activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83, 329, 412, 416, 417, 418, 419, 420, 423, 425, 428, 431, 457, 464, 471, 472, 475, 645, 795, 797, 798, 799, 800, 809, 823 and 837.

The compounds A and B exhibited the curative activity value "0".

Biological Test Example 9

Preventive test against powdery mildew on grape

A plastic pot was filled with sandy loam, and grape (Berry

A) was seeded and raised in a greenhouse for 1.5 months. Suspensions prepared from a test compound in the same manner as described in Formulation Example 2 were diluted with water to the predetermined concentration of 500 ppm and the resulting solution was sprayed over the stem and leaves so as to sufficiently adhere to the leaf surface of the grape seedlings. Then the grape seedlings were air-dried and inoculated with a spore solution of Uncinula necator by spraying. After the inoculation, the grape seedlings were raised in a greenhouse at 25° C. for 14 days and the control effect was examined. As a result, the following compounds exhibited the preventive activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83 and 329.

The compounds A and B exhibited the preventive activity value "0".

Biological Test Example 10

Preventive test against gray mold on cucumber

A plastic pot was filled with sandy loam, and cucumber (Sagamihanjiro) was seeded and raised in a greenhouse for 7 days. Wettable powders prepared from a test compound in the same manner as described in Formulation Example 1 were diluted with water to the predetermined concentration of 500 ppm and the resulting solution was sprayed over the stem and leaves so as to sufficiently adhere to the leaf surface of the cucumber seedlings. Then the cucumber seedlings were inoculated with a spore solution of the pathogen by spraying. After the inoculation, the cucumber seedlings were raised at 10° C. under dark and high humidity for 4 days and the control effect was examined. As a result, the following compounds exhibited the preventive activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83, 329, 412, 414, 416, 417, 418, 419, 420, 421, 423, 425, 428, 431, 457, 459, 462, 464, 471, 472, 475, 485, 645, 795, 797, 798, 799, 800, 809, 823 and 837.

The compounds A and B exhibited the preventive activity value "0".

Biological Test Example 11

Preventive test against scab on apples

A plastic pot was filled with sandy loam, and apple (Fuji) was seeded and raised in a greenhouse for 20 days. Suspensions prepared from a test compound in the same manner as described in Formulation Example 2 were diluted with water to the predetermined concentration of 500 ppm and the resulting solution was sprayed over the stem and leaves so as to sufficiently adhere to the leaf surface of the apple seedlings where the fourth or fifth true leaf was put out. After the solution was sprayed, a spore solution of Venturia inaequalis was sprayed and dried. After the inoculation, the apple seedlings were maintained at 15° C. under dark and high humidity and raised under lighting for additional 15 days and the control effect was examined. As a result, the following compounds exhibited the preventive activity value "5".

Compound Nos. 1, 2, 3, 6, 7, 9, 10, 18, 19, 21, 26, 30, 31, 32, 33, 42, 48, 50, 52, 55, 62, 72, 74, 76, 77, 78, 79, 80, 81, 82, 83 and 329.

The compounds A and B exhibited the preventive value "0".

Biological Test Example 12

Preventive test against powdery mildew on cucumber

A plastic pot was filled with sandy loam, and cucumber (Sagamihanjiro) was seeded and raised in a greenhouse for 7 days. Wettable powders prepared from a test compound in the same manner as described in Formulation Example 1 were diluted with water to the predetermined concentration of 500 ppm and the resulting solution was sprayed over the stem and leaves so as to sufficiently adhere to the leaf surface of the cucumber seedling. Then a spore solution was sprayed onto the cucumber seedlings to inoculated them with the pathogen. After the inoculation, the cucumber seedlings were raised at 25° C. under dark and high humidity for 14 days and the control effect was examined. As a result, the following compounds exhibited the preventive activity value "5".

Compound Nos. 412, 416, 417, 418, 419, 420, 423, 428, 431, 457, 459, 464, 472, 475, 645, 795, 797, 798, 799, 800, 809, 823 and 837.

The following will describe several examples of an insecticidal/acaricidal test.

Biological Test Example 13

Insecticidal test against *Aphis gossypii* Glover

First, 20 larvae of *Aphis gossypii* Glover per leaf were allowed to parasitize a potted cotton grown for 7 days after seeding. Then, emulsifiable concentrates prepared from a test compound in the same manner as described in Formulation Example 4 were diluted with water to the predetermined concentration of 50 ppm and 15 ml of the resulting solution was sprayed over each pot, respectively, on a turn table. After 7 days, the number of survived *Aphis gossypii* Glover was examined.

As a result, no survival larvae were observed in cotton treated with the compounds 10, 19, 21, 26, 31, 48, 50, 74, 77, 78, 79, 416, 417, 418, 420, 475, 645, 796, 797, 798, 800, 809, 823 and 837.

Biological Test Example 14

Insecticidal Test against brown house mosquito

First, emulsifiable concentrates prepared from a test compound in the same manner as described in Formulation Example 4 were diluted with water to the predetermined concentration of 500 ppm. Then, 0.7 ml of this solution was added to 100 ml of deionized water (concentration of an active ingredient: 3.5 ppm). Then, 20 larvae (last instar) of Brown house mosquito were set free. After 8 days, an inhibition rate of hatching was examined.

As a result, the compounds 3, 7, 9, 10, 18, 19, 26, 31, 42, 48, 50, 77, 78, 79, 80, 416, 418, 475, 795, 797, 799, 809, 823 and 837 exhibited the inhibition ratio of 90% or more.

Biological Test Example 15

Acaricidal Test against *Tetranychus cinnabarius*

First, 10 female adults of *Tetranychus cinnabarius* per leaf were allowed to parasitize a potted bean grown for 7 days after seeding (primary leaf stage), which was placed in a greenhouse maintained at 25° C. After 6 days, emulsifiable concentrates prepared from a test compound in the same manner as described in Formulation Example were diluted with water to the predetermined concentration of 500 ppm. This solution (15 ml) was sprayed over each pot, respectively, on a turn table. At the same time, 2 ml of the same solution was drenched in the soil. After 8 days, the degree of damage of the respective plants caused by spider mite was evaluated according to the following criteria:

"–": Damage was scarcely observed.

"+": A little damage was observed.

"++": Damage similar to that found in the non-treated field was observed.

As a result, the compounds 7, 10, 19, 21, 31, 48, 50, 77, 78, 79, 418, 420, 431, 795, 797, 798, 799, 809, 823 and 837 were evaluated as "−".

Biological Test Example 16

Insecticidal Test against cut worm

First, 13 g of artificial bait put in a polyethylene cup (diameter, 11 cm) was impregnated with a solution prepared from the emulsifiable concentrates according to Formulation Example 4. Ten larvae of 4-stage instar of *Spodoptera litura* were set free in the cup. After 6 days, the mortality of the larvae was examined.

As a result, no survival larvae were observed in cups treated with the compounds 799, 809, 823 and 837.

Biological Test Example 17

Insecticidal Test against brown rice plant hopper

Stalks of rice seedlings (length, 5 cm) were dipped for 1 minute in a solution prepared from emulsifiable concentrates according to Formulation Example 4. After the stalks were air-dried, they were put in a polyethylene cup (diameter, 5.5 cm) in which filter paper (diameter, 5 cm) soaked with 1 ml of water was placed.

About 30 larvae of *Nilaparvata lugens* were set free in the cup, and the activity of the test compound was examined according to the following criteria:

a: No surviving larvae were observed.

b: 5 or less larvae were surviving.

c: 6 or more larvae were surviving.

As a result, no survival larvae were observed in cups treated with the compounds 425, 797, 823 and 837, while untreated control was evaluated as "c".

What is claimed is:

1. A dithiocarbonimide derivative of the formula I:

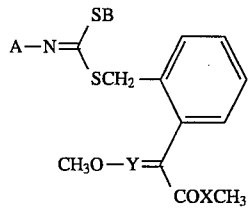

wherein B is a $C_1$–$C_6$ alkyl group; X is an NH group and Y is a nitrogen atom; A is a phenyl group, a heterocyclic group, an alkyl group, an alkenyl group, an alkynyl group, a cycloalkyl group, a cycloalkenyl group, a bicycloalkyl group or a tricycloalkyl group, all of which may be substituted.

2. A dithiocarbonimide derivative according to claim 1, wherein X is an NH group and Y is a nitrogen atom, A is a phenyl group, a heterocyclic group of which carbon atom is bonded to the imino nitrogen atom, an alkyl group, an alkenyl group, alkynyl group, a cycloalkyl group, a cycloalkenyl group, a bicycloalkyl group or a tricycloalkyl group, all of which may be substituted.

3. A dithiocarbonimide derivative according to claim 2, wherein A is a phenyl group or a heterocyclic group, both of which may be substituted with a $C_1$–$C_6$ alkyl group, a halogen atom, a $C_1$–$C_6$ alkoxy group, a phenoxy group, a $C_1$–$C_6$ alkylthio group, an ($C_1$–$C_6$)alkyloxycarbonyl group, a cyano group, a nitro group, a $C_1$–$C_6$ haloalkyl group, a $C_1$–$C_6$ haloalkoxy group or a methylenedioxy group which may be substituted with a fluorine atom; or A is a $C_1$–$C_{20}$ alkyl group, a $C_2$–$C_{20}$ alkenyl group, a $C_2$–$C_{20}$ alkynyl group, a $C_3$–$C_{20}$ cycloalkyl group, a $C_5$–$C_{20}$ cycloalkenyl group, a $C_4$–$C_{20}$ bicycloalkyl group or a $C_4$–$C_{20}$ tricycloalkyl group, all of which may be substituted.

4. A dithiocarbonimide derivative according to claim 3, wherein A is a $C_1$–$C_{10}$ alkyl group, a $C_2$–$C_{10}$ alkenyl group, a $C_2$–$C_{10}$ alkynyl group, a $C_3$–$C_{10}$ cycloalkyl group, a $C_5$–$C_{10}$ cycloalkenyl group, a $C_4$–$C_{10}$ bicycloalkyl group or a $C_4$–$C_{10}$ tricycloalkyl group, all of which may be substituted.

5. A dithiocarbonimide derivative according to claim 4, wherein the $C_1$–$C_{10}$ alkyl group which may be substituted is a methyl group, an ethyl group, a propyl group, a butyl group, a pentyl group, a hexyl group, a heptyl group, an octyl group, a nonyl group, a decyl group, a 1-methylethyl group, a 1-methylpropyl group, a 2-methylpropyl group, a 1,1-dimethylethyl group, a 1-methylbutyl group, a 1-ethylpropyl group, a 2-methylbutyl group, a 3-methylbutyl group, a 2,3-dimethylbutyl group, a 1,3-dimethylbutyl group, a 3,3-dimethylbutyl group, a 1-methylpentyl group, a 1-ethylpentyl group, a 1-methylhexyl group, a 2-ethylhexyl group or a 1,5-dimethylhexyl group.

6. A dithiocarbonimide derivative according to claim 4, wherein the $C_1$–$C_{10}$ alkyl group which may be substituted is a group of the formula:

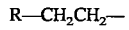

R is a tert-butyl group, an isopropyl group or a phenyl group which may be substituted with at least one group selected from a halogen atom, a $C_1$–$C_4$ alkyl group, a $C_1$–$C_4$ alkylthio group, a $C_1$–$C_4$ haloalkyl group, a $C_1$–$C_4$ haloalkoxy group and a cyano group.

7. A dithiocarbonimide derivative according to claim 1, wherein the substituents on the alkyl group, alkenyl group, alkynyl group, cycloalkyl group, cycloalkenyl group, bicycloalkyl group or tricycloalkyl group may be the same or different and are three or less groups selected from the group consisting of a methoxy group, an ethoxy group, an n-propoxy group, an isopropoxy group, an n-butoxy group, a t-butoxy group, a trifluoromethoxy group, a 2,2,2-trifluoroethoxy group, a 2,2,2,2', 2',2'-hexafluoroisopropoxy group, a fluorine atom, a chlorine atom, a bromine atom, an iodine atom, a cyano group, a methylthio group, an ethylthio group, a phenyl group, a phenoxy group, a phenylthio group, a 2-furyl group, a 2-thienyl group, a 1-imidazolyl group, a 2-imidazolyl group, a 2-pyridyl group, a 3-pyridyl group, a 4-pyridyl group, a cyclopropyl group, a cyclobutyl group, a cyclopentyl group, a cyclohexyl group, a tetrahydrofuryl group, a tetrahydropyranyl group and a 4-morpholinyl group, wherein the phenyl group, phenoxy group, phenylthio group, 2-furyl group, 2-thienyl group, 1-imidazolyl group, 2-imidazolyl group, 2-pyridyl group, 3-pyridyl group, 4-pyridyl group, a cyclopropyl group, a cyclobutyl group, a cyclopentyl group, a cyclohexyl group, a tetrahydrofuryl group, a tetrahydropyranyl group and a 4-morpholinyl group may be substituted with three or less groups which are same or different and are selected from the group consisting of a methyl group, an ethyl group, an n-propyl group, an isopropyl group, a trifluoromethyl group, a methoxy group, an ethoxy group, an n-propoxy group, an isopropoxy group, a trifluoromethoxy group, a fluorine atom, a chlorine atom, a bromine atom, an iodine atom, a cyano group, a nitro group, a methylthio group and an ethylthio group.

8. A dithiocarbonimide derivative according to claim 3, wherein the heterocyclic group which may be substituted is a pyridyl group, a pyrimidinyl group, a pyridazinyl group, a pyrazolyl group, an imidazolyl group, an oxazolyl group, a thiazolyl group, an isothiazolyl group, a triazolyl group or a thiadiazolyl group.

9. A dithiocarbonimide derivative according to claim 4, wherein the alkenyl group which may be substituted is an allyl group or a 2-methylallyl group; the alkynyl group which may be substituted is a propargyl group; the cycloalkyl group which may be substituted is a cyclopropyl group, a cyclobutyl group, a cyclopentyl group, a cyclohexyl group, a cycloheptyl group, a cyclooctyl group or a cyclodecyl group; the cycloalkenyl group which may be substituted is a cyclopentenyl group or a cyclohexenyl group; the bicycloalkyl group which may be substituted is an exo-2-norbornyl group or an endo-2-norbornyl group; or the tricycloalkyl group which may be substituted is a 1-adamantyl group or a 2-adamantyl group.

10. A dithiocarbonimide derivative according to claim 1, wherein B is a methyl group.

11. A dithiocarbonimide derivative according to claim 1, which is N-(4-ethylphenyl)-S-methyl-S-(2-(α-methoxyimino-α-N'-methylcarbamoylmethyl)-phenylmethyl)dithiocarbonimide of the formula:

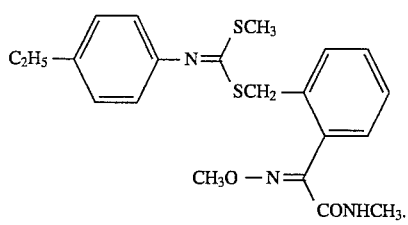

12. A dithiocarbonimide derivative according to claim 1, which is N-(4-trifluoromethylphenyl)-S-methyl-S-(2-(α-methoxyimino-α-N'-methylcarbamoylmethyl)phenylmethyl)dithiocarbonimide of the formula:

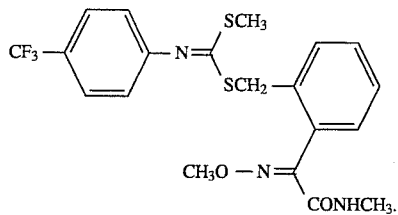

13. A dithiocarbonimide derivative according to claim 1, which is N-(2-ethoxypyridin-5-yl)-S-methyl-S-(2-(α-methoxyimino-α-N'-methylcarbamoylmethyl)phenylmethyl)dithiocarbonimide of the formula:

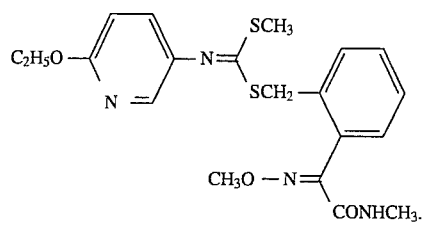

14. A dithiocarbonimide derivative according to claim 1, which is N-(4-ethoxyphenyl)-S-methyl-S-(2-(α-methoxyimino-α-N'-methylcarbamoylmethyl)phenylmethly)dithiocarbonimide of the formula:

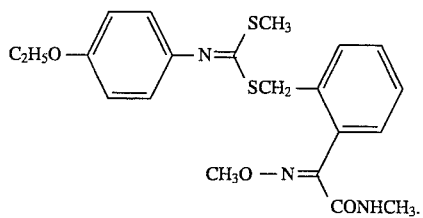

15. A method of controlling noxious insects or acarines, which comprises applying an insecticically or acaricidally effective amount of a dithiocarbonimide derivative according to claim 1 to a locus where the noxious insects or acarines propagate.

16. A fungicidal, insecticidal or acaricidal composition comprising an fungicidally, acaricidally or insecticidally effective amount of a dithiocarbonimide derivative according claim 1 as an active ingredient, and an inert carrier or diluent.

* * * * *